US010933207B2

(12) United States Patent
Huber et al.

(10) Patent No.: US 10,933,207 B2
(45) Date of Patent: Mar. 2, 2021

(54) DRUG DELIVERY APPARATUS

(71) Applicant: ASMEDIC LTD., Haifa (IL)

(72) Inventors: Arie Huber, Haifa (IL); Valentin Nov, Haifa (IL)

(73) Assignee: ASMEDIC LTD., Haifa (IL)

( * ) Notice: Subject to any disclaimer, the term of this patent is extended or adjusted under 35 U.S.C. 154(b) by 896 days.

(21) Appl. No.: 15/328,618

(22) PCT Filed: Jun. 28, 2015

(86) PCT No.: PCT/IB2015/054853
§ 371 (c)(1),
(2) Date: Jan. 24, 2017

(87) PCT Pub. No.: WO2016/030777
PCT Pub. Date: Mar. 3, 2016

(65) Prior Publication Data
US 2017/0216539 A1    Aug. 3, 2017

Related U.S. Application Data

(60) Provisional application No. 62/041,951, filed on Aug. 26, 2014.

(51) Int. Cl.
*A61M 15/00* (2006.01)
*A61B 5/00* (2006.01)
(Continued)

(52) U.S. Cl.
CPC ......... *A61M 15/0066* (2014.02); *A61B 5/087* (2013.01); *A61B 5/0873* (2013.01);
(Continued)

(58) Field of Classification Search
CPC .......... A61M 15/0066; A61M 15/0018; A61M 15/0085; A61M 15/0043; A61M 16/024;
(Continued)

(56) References Cited

U.S. PATENT DOCUMENTS

| 5,450,336 A | 9/1995 | Rubsamen et al. |
| 5,522,380 A | 6/1996 | Dwork |

(Continued)

FOREIGN PATENT DOCUMENTS

| EP | 0824023 A1 | 2/1998 |
| GB | 2354451 A | 3/2001 |

(Continued)

OTHER PUBLICATIONS

International Search Report in PCT/IB2015/0548353 dated Oct. 22, 2015.

(Continued)

*Primary Examiner* — Colin W Stuart
*Assistant Examiner* — Douglas Y Sul
(74) *Attorney, Agent, or Firm* — Manelli Selter PLLC; Edward Stemberger

(57) ABSTRACT

A personalized drug delivery apparatus including drug containing structure; a spout configured to receive full lung exhalation; a mechanism configured to determine a personalized drug dosage according to the exhalation, the spout further configured to enable inhalation of the determined dosage.

8 Claims, 22 Drawing Sheets

(51) Int. Cl.
 *A61B 5/087* (2006.01)
 *A61M 16/00* (2006.01)
(52) U.S. Cl.
 CPC .......... *A61B 5/4839* (2013.01); *A61B 5/4845* (2013.01); *A61M 15/0018* (2014.02); *A61M 16/024* (2017.08); *A61M 15/0043* (2014.02); *A61M 15/0085* (2013.01); *A61M 2016/0027* (2013.01); *A61M 2016/0042* (2013.01); *A61M 2202/064* (2013.01); *A61M 2205/18* (2013.01); *A61M 2205/3365* (2013.01); *A61M 2205/50* (2013.01); *A61M 2205/505* (2013.01); *A61M 2205/52* (2013.01); *A61M 2205/8206* (2013.01)
(58) Field of Classification Search
 CPC .. A61M 2016/0027; A61M 2016/0042; A61M 2205/50; A61M 2205/52; A61M 5/4839; A61M 5/087
 See application file for complete search history.

(56) References Cited

U.S. PATENT DOCUMENTS

| | | | |
|---|---|---|---|
| 5,769,073 A | 6/1998 | Eason et al. | |
| 6,234,167 B1 * | 5/2001 | Cox | A61M 15/0003 128/200.14 |
| 6,422,234 B1 | 7/2002 | Bacon | |
| 8,869,793 B1 * | 10/2014 | Spandorfer | A61B 5/082 128/203.14 |
| 2002/0053344 A1 | 5/2002 | Davies et al. | |
| 2004/0118398 A1 | 6/2004 | Huber et al. | |
| 2009/0156952 A1 * | 6/2009 | Hunter | A61M 16/024 600/538 |
| 2009/0178672 A1 | 7/2009 | Mullinger et al. | |
| 2009/0188498 A1 | 7/2009 | Thoemmes et al. | |
| 2012/0186582 A1 | 7/2012 | Addington et al. | |
| 2012/0291781 A1 | 11/2012 | Kaufmann et al. | |
| 2013/0255678 A1 * | 10/2013 | Gumaste | A61M 15/0065 128/203.15 |
| 2014/0116426 A1 * | 5/2014 | Mullinger | A61M 11/005 128/200.14 |
| 2015/0290418 A1 * | 10/2015 | Kaczka | A61M 16/18 128/200.14 |

FOREIGN PATENT DOCUMENTS

| | | |
|---|---|---|
| WO | 90/07351 A1 | 7/1990 |
| WO | 9848873 A1 | 11/1998 |
| WO | 2012026963 A | 3/2012 |

OTHER PUBLICATIONS

International Preliminary Report on Patentability in PCT/IB2015/054853 dated Dec. 6, 2016.

* cited by examiner

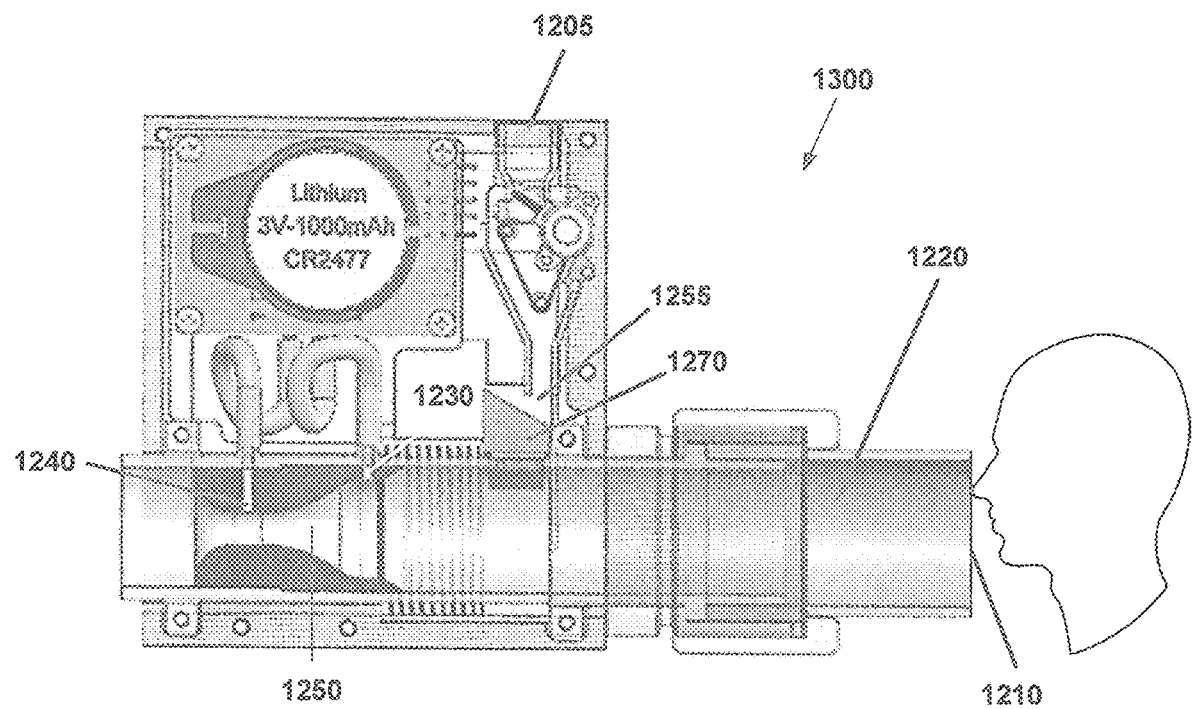
Fig. 13
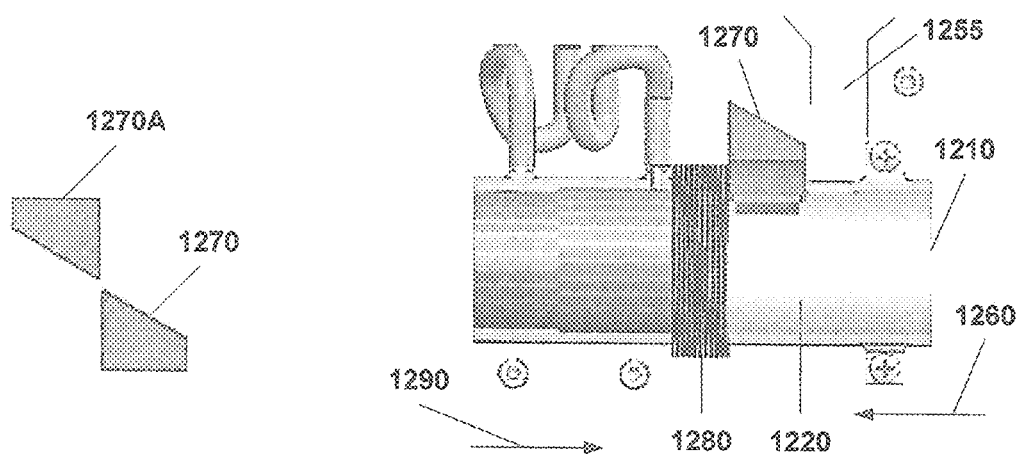
Fig. 13B
Fig. 13A

DRUG DELIVERY APPARATUS

CROSS-REFERENCE TO RELATED PATENT APPLICATIONS

This patent application claims priority from and is related to U.S. Provisional Patent Application Ser. No. 62/041,951, filed 26 Aug. 2014, this U.S. Provisional Patent Application incorporated by reference in its entirety herein.

FIELD OF THE INVENTION

The present invention generally relates to drug delivery systems and specifically to an adaptive personalized drug dosage delivery apparatus.

BACKGROUND

An inhaler (or puffer) is a medical device used for delivering medication into the body via the lungs. It is mainly used in the treatment of asthma and Chronic Obstructive Pulmonary Disease (COPD).

To reduce deposition in the mouth and throat, and to reduce the need for precise synchronization of the start of inhalation with actuation of the device, MDIs are sometimes used with a complementary spacer or holding chamber device.

Decongestant inhalers are popular over-the-counter remedies for nasal congestion in the upper respiratory tract.

The most common type of inhaler is the pressurized metered-dose inhaler (MDI). In MDIs, medication is typically stored in solution in a pressurized canister that contains a propellant, although it may also be a suspension. The MDI canister is attached to a plastic, hand-operated actuator. On activation, the metered-dose inhaler releases a fixed dose of medication in aerosol form. The correct procedure for using an MDI is to first fully exhale, place the mouth-piece of the device into the mouth, and having just started to inhale at a moderate rate, depress the canister to release the medicine. The aerosolized medication is drawn into the lungs by continuing to inhale deeply before holding the breath for 10 seconds to allow the aerosol to settle onto the walls of the bronchi and other airways of the lung. Some inhalers are made to act before an asthma attack, some are made to act instantly in case of an asthma attack and others are made to act later.

Another type of inhaler is a dry powder inhaler (DPI). Dry powder inhalers release a metered or device-measured dose of powdered medication that is inhaled through a DPI device.

Existing inhalers are configured to release a predetermined drug dosage.

There is a long felt need for a drug delivery apparatus which enables to provide a personalized drug dosage to a patient according to his respiratory flow.

SUMMARY

According to an aspect of the present invention there is provided a personalized drug delivery apparatus comprising: drug containing means; a spout configured to receive full lung exhalation; a mechanism configured to determine a personalized drug dosage according to the exhalation, the spout further configured to enable inhalation of the determined dosage.

The drug containing means may comprise one of compartment, individual cells and strip.

The drug containing means may be replaceable.

The replaceable drug containing means may be a capsule.

The mechanism may comprise a drug release mechanism.

The mechanism may further comprise a sensor configured to measure the exhalation; and a controller configured to determine the drug dosage according to the measured exhalation; wherein the drug release mechanism may comprise a valve configured to enable: a. the exhalation and b. inhalation of the personalized drug dosage.

The mechanism may further comprise a first sensor mounted in the narrowest part of a venturi nozzle and configured to measure the exhalation; a second sensor mounted in the widest part of the venturi nozzle and configured to measure the exhalation; and a controller configured to determine the drug dosage according to the measurements.

The release mechanism may comprise a pump and an air source.

The release mechanism may comprise an actuator connected with a disk; the actuator may be configured to move the disk which opens at least one individual cell containing drug, according to the determined drug dosage.

The release mechanism may comprise a peeling mechanism configured to peel the drug from a strip.

The release mechanism may comprise a spiral mounted in a drug compartment; the spiral having slots and configured to rotate and release drug according to the personalized dosage.

The id release mechanism may comprise two moveable parts mounted in a calculated distance from each other; the calculated distance may be configured to be mounted under the drug containing means and to be filled with the drug dosage; and the two moveable parts are configured to move together and release the drug dosage.

The release mechanism may comprise an actuator configure to actuate a conveyor mounted under the drug containing means; the drug lays on the conveyor which may be configured to move and release the drug through an orifice.

The release mechanism may comprise a nozzle configured to connect the drug containing means with a cavity; the release mechanism may be configured to release drug from the drug containing means through the nozzle and into the cavity.

The cavity may comprise a fixed size cavity and an adjustable size cavity.

The adjustable size cavity volume may be changed by one of an actuator and manually.

The release mechanism may comprise an actuator configured to move a piston; the piston may be configured to suck the drug from the drug containing means.

The mechanism may comprise a flap configured to be push by the exhalation and to indicate the personalized drug dosage accordingly.

The mechanism may comprise a wind cup configured to be pushed by the exhalation and determine the personalized drug dosage.

The mechanism may further comprise a propeller configured to actuate the release mechanism when a patient blows toward it.

According to another aspect of the present invention there is provided a method of delivering a personalized drug dosage comprising: performing a test comprising measuring full-lung exhalation through a spout; determining a personalized drug dosage according to the test; and releasing the personalized drug dosage according to the determination.

The releasing may comprise opening a valve connecting a drug compartment with the spout.

The releasing may comprise activating a pump and an air source.

The releasing may comprise activating an actuator which opens individual cells.

The releasing may comprise peeling the drug dosage from a strip.

The releasing may comprise rotating a spiral having slots filled with drug.

The determining may comprise calculating a distance between a first moveable part and a second moveable part.

The releasing may comprise moving the two movable parts.

The releasing may comprise actuating a conveyor.

The releasing may further comprise pushing a spout.

The determining may comprise activating an actuator configured to control an adjustable cavity's size.

The determining may comprise rotating a screw configured to control an adjustable cavity's size.

The releasing may comprise activating an actuator configured to: a. pull a piston and b. push a piston.

The releasing may comprise: a. pulling a piston and b. pushing a piston.

The determining may comprise rotating a dial.

The steps of performing a test, determining and releasing may comprise blowing towards a propeller; the propeller may actuate a release mechanism.

BRIEF DESCRIPTION OF THE DRAWINGS

For better understanding of the invention and to show how the same may be carried into effect, reference will now be made, purely by way of example, to the accompanying drawings.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings:

FIG. 13 is a schematic view of another exemplary drug delivery apparatus according to embodiments of the present invention;

FIG. 13A describes the inhalation stage of the process described in conjunction with the apparatus of FIG. 13;

FIG. 13B demonstrates a slant configured to assist in releasing the drug;

DETAILED DESCRIPTION OF PREFERRED EMBODIMENTS

Figure 1:
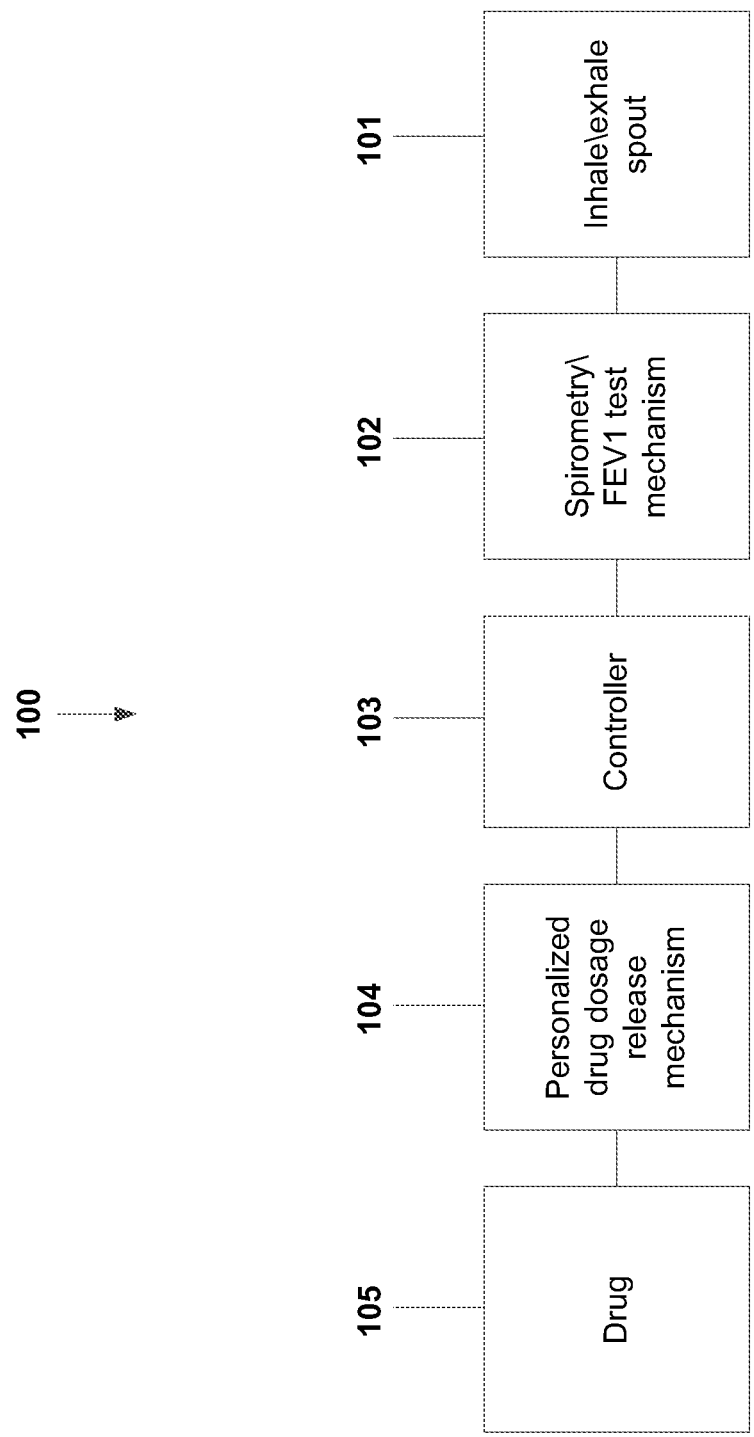
FIG. 1 shows a schematic block diagram of the drug delivery apparatus according to embodiments of the invention.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

The present invention provides an apparatus and method for adjusting and providing a personalized drug dosage to a patient having asthma or a Chronic Obstructive Pulmonary Disease (COPD). The apparatus measures the patient's respiratory flow and adjusts and provides a personalized drug dosage to him accordingly.

FIG. 1 shows a schematic block diagram of the drug delivery apparatus 100 components according to embodiments of the invention comprising an inhale\exhale spout 101, a spirometry\FEV1 test mechanism 102, a personalized drug dosage release mechanism 104, drug 105 and a controller 103 configured to control the spirometry\FEV1 test mechanism 102, determine a personalized drug dosage according to the test and control the personalized drug dosage release mechanism 104.

Figure 2:
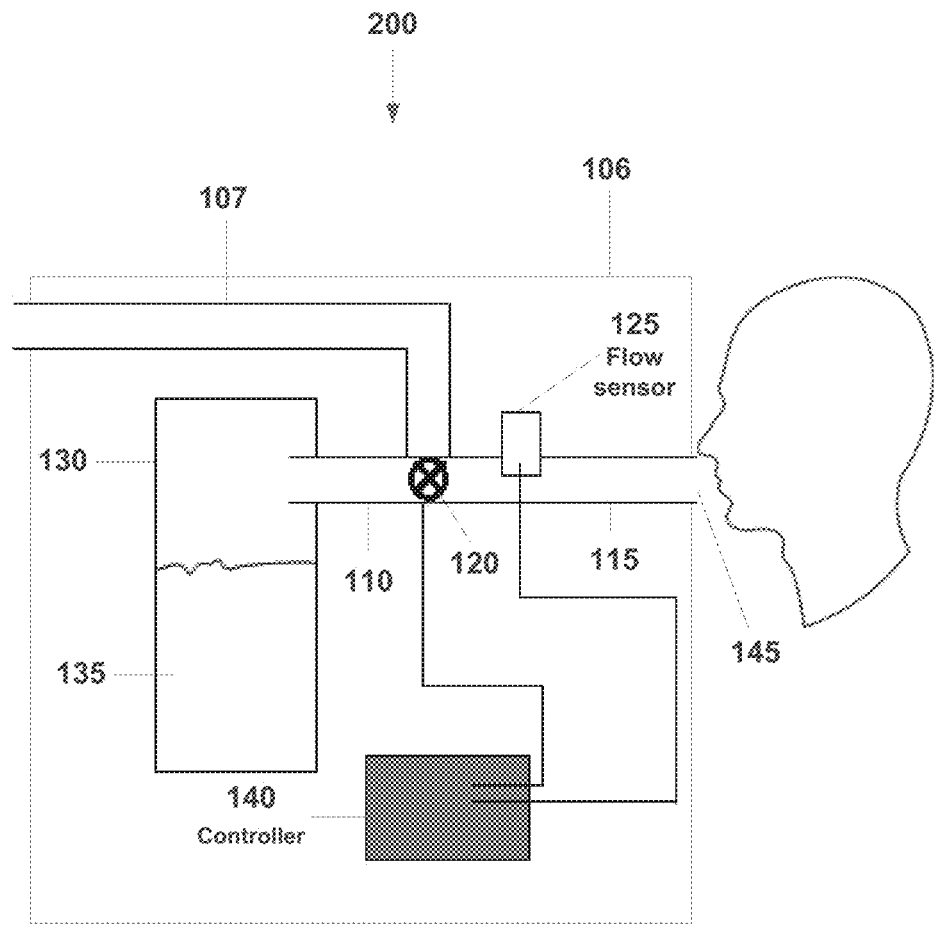
FIG. 2 shows an exemplary delivery apparatus according to embodiments of the present invention.

FIG. 2 shows an exemplary delivery apparatus 200 according to embodiments of the present invention comprising: a housing 106 comprising a medicine compartment 130 storing medicine powder 135 (drug), a first tube 107 connected to a second tube 110 and a third tube 115 through a drug release mechanism implemented by a valve 120, a test mechanism implemented by a flow sensor 125 mounted in the third tube 115, an ON\OFF switch (not shown), an actuator (not shown) configured to move the valve 120 and a controller 140 configured to control the flow sensor 125 and the valve 120 actuator and to enable full operation of the apparatus.

The apparatus 200 may further comprise a plastic cover (not shown) configured to cover the inhale\exhale spout 145 mounted at the end of the third tube 115 and a status LED (not shown) which indicates the apparatus's status. For example: Off—the apparatus is off; Red—Fault—reset the apparatus or if the reset didn't work, do not use the apparatus; Yellow—perform a spirometry\FEV1 (Forced Expiratory Volume) test; Green—Inhale the medicine (drug).

According to embodiments of the invention, the medicine compartment 130 may be a replaceable compartment.

The flow sensor 125 (test mechanism) comprises a transducer which may be implemented by, but is not limited to the following techniques:

Piezo resistive technique:
  A piezo resistive pressure or very common air-turbine technique.
  The transducer's output is a variable impedance signal.
  The transducer's output signal is detected by an analog detector.
  The Analog detector's output is a low voltage analog signal.
Infra Red (IR) technique:
  Based on detection and counting of an IR reflection signals.
  The number of reflections during the counting period is proportional to the airflow speed.
Reverse turbine effect:
  An impeller attached to an encoding wheel counts speed, rate and direction, thus it dynamically measures the airflow.
  The encoder records its data into a microprocessor unit to be further converted into a precise motor RPM unit counter to deploy powder.
Pitot tube pressure gauge:
  This method is based on pressure measured along a tiny orifice.
  By monitoring the FEV1 indicator, a microprocessor, calculates drug amounts required.

The controller 140 may comprise an A\D converter, Central processing unit (CPU), Real-time clock (RTC), Memory, RS-232 driver, USB driver, RFID driver and WIFI driver.

The controller may additionally comprise an MP3/MP4 media player and\or an LCD driver.

The A\D converter converts analog signal(s), received from the sensor, to digital signal(s).

The CPU uses the digital signal(s) to verify the FEV1 and according to the result, determines the proper drug dosage.

The FEV1, details of used drug dosage and related time stamp may be stored in a memory as history.

According to embodiments of the invention, if the CPU does not receive any signal for a predefined period of time, the apparatus switches to a sleep or latent mode for power saving purposes.

The unit includes BIT process for majority of the apparatus's modules and Low Battery indication.

Figure 3:
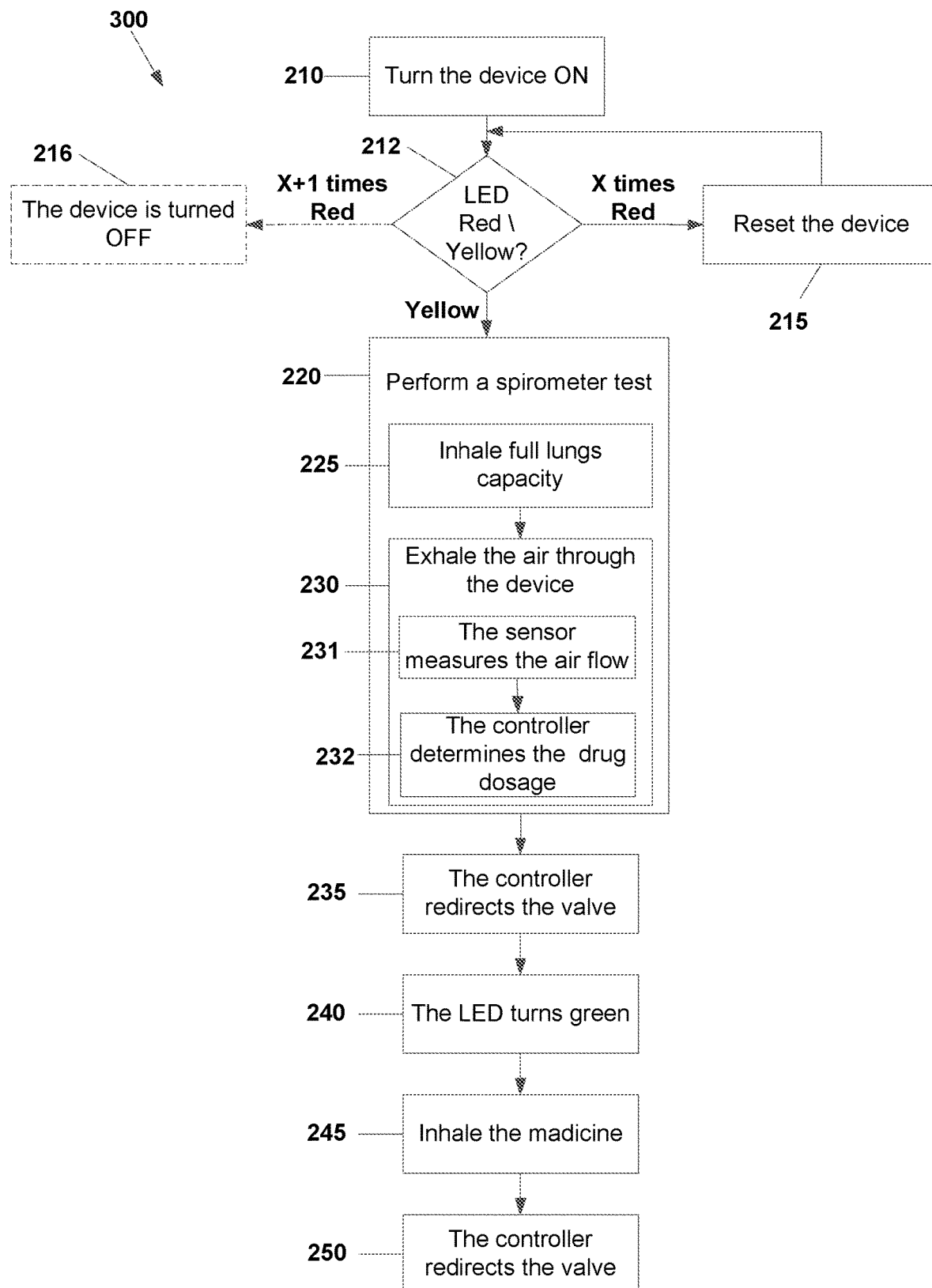
FIG. 3 is a flowchart showing the process performed by a patient who uses the delivery apparatus of FIG. 2.

FIG. 3 is a flowchart 300 showing the process performed by a patient who uses the delivery apparatus 200 of FIG. 2 according to embodiments of the present invention. At the beginning of the process, the valve (release mechanism) 120 connects the first tube 107 with the third tube 115. In step 210, the patient turns the apparatus ON. If in step 212 the LED turns red (within a predefined X times it is allowed to be red), in step 215, reset the apparatus. If the reset didn't work X+1 times (the LED continues to be red), the apparatus is turned OFF, namely, do not use the apparatus or check it. If in step 212 the LED turns yellow, in step 220, perform the spirometer test. The spirometer test includes two stages, in the first stage—225, the patient inhales full lung capacity (not through the apparatus) and in the second stage—230, he exhales the air through the apparatus for at least 1.5 sec. During the second stage, in step 231, the flow sensor (test mechanism) 125 measures the air flow and in step 232, the controller 140 calculates the FEV1 and determines the patient's needed drug dosage accordingly. When the test is completed, in step 235, the controller redirects the valve 120 to connect the second tube 110 to the third tube 115, in step 240, the LED turns green and in step 245 the patient may inhale the medicine (drug) through the inhale\exhale spout. In step 250, the controller redirects the valve 120 to connect the first tube 107 to the third tube 115 according to the determined dosage in order to stop the medicine flow.

According to a predefined calibration table the ratio between the FEV1 and the medicine quantity is predefined—Q*

Q may be calculated as follows:

$$Q = \int_{t_1}^{t_0} F*A*C$$

Where:
A=the tube (115) area.
F=the flow
C=the medicine concentration.
$T_0$=the starting time when the patient starts to inhale.
$T_1$=is defined as the time when Q=Q*.

According to embodiments of the invention, X is determined by the apparatus's manufacturer.

According to embodiments of the invention, prior to the process of FIG. 3, the patient may have to input his weight, age, height and sex for the apparatus to know the anticipated limits of the spirometry test.

Figure 4:
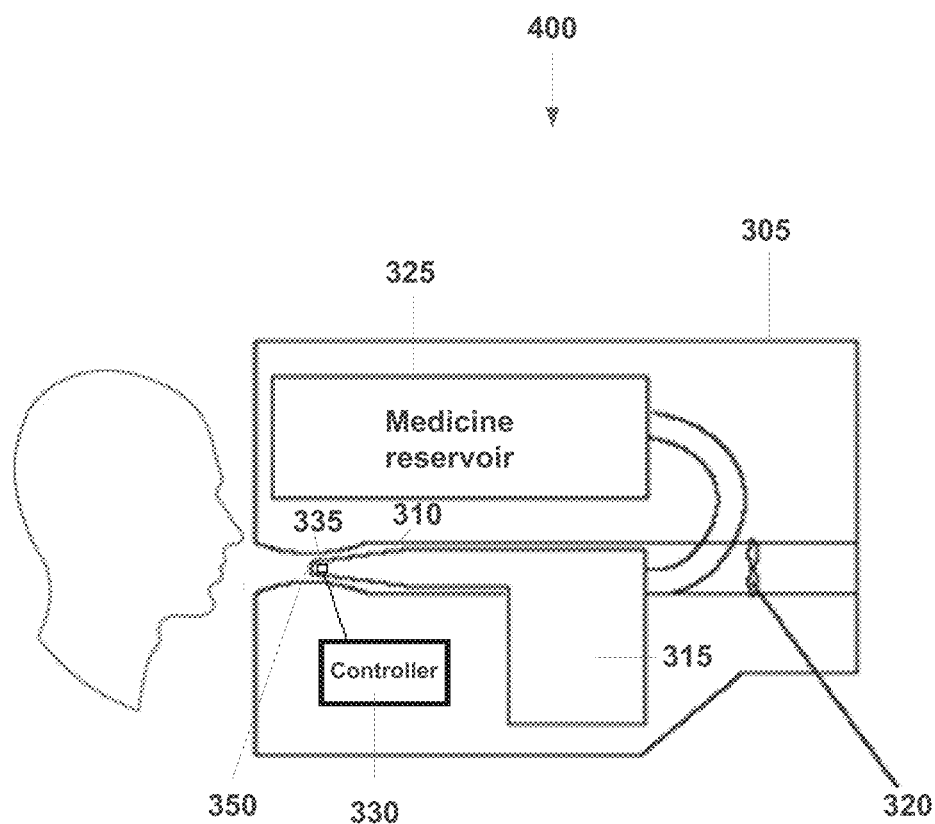
FIG. 4 shows another exemplary delivery apparatus according to embodiments of the present invention.

FIG. 4 shows another exemplary delivery apparatus 400 according to embodiments of the present invention comprising: a housing 305 comprising a medicine reservoir 325 storing medicine (drug) (not shown), a test mechanism implemented by a Venturi nozzle 310 and a flow sensor 335 mounted in the Venturi nozzle 310, the venturi nozzle is connected with the medicine reservoir (compartment) 325, a release mechanism implemented by a piezo-electric pump 315 and an air source 320 (such as a fan, compressed air, etc.), an optional air flow monitor (not shown) and a controller 330 connected with the test mechanism and the release mechanism. An inhale\exhale spout (not shown) is connected to the end 350 of the venturi nozzle 310.

According to embodiments of the invention, the medicine reservoir 325 may be a replaceable reservoir.

Figure 5:
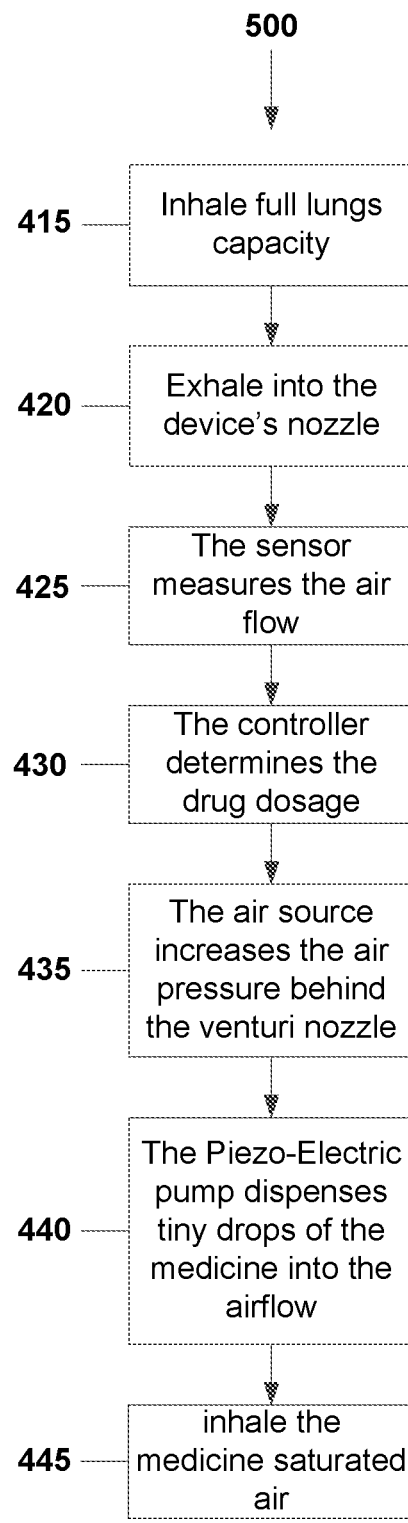
FIG. 5 is a flowchart showing the process performed by a patient who uses the delivery apparatus of FIG. 4.

FIG. 5 is a flowchart 500 showing the process performed by a patient who uses the delivery apparatus 400 of FIG. 4 according to embodiments of the invention. In step 415, the patient inhales full lungs capacity (not through the apparatus). In step 420, the patient exhales through the spout into the nozzle 310. In step 425, the velocity and quantity of air is measured by the sensor 335. In step 430, the measured air is compared with predefined values and the controller 330 determines the amount of medicine to dispense accordingly. In step 435, the air source 320 increases the air pressure behind the venturi nozzle. In step 440, The Piezo-Electric pump 315 dispenses in rapid succession tiny drops of the medicine into the airflow. These drops may be broken into even smaller drops due to the increased air velocity in the venturi nozzle. In step 445, the patient inhales the medicine saturated air.

Figure 6:
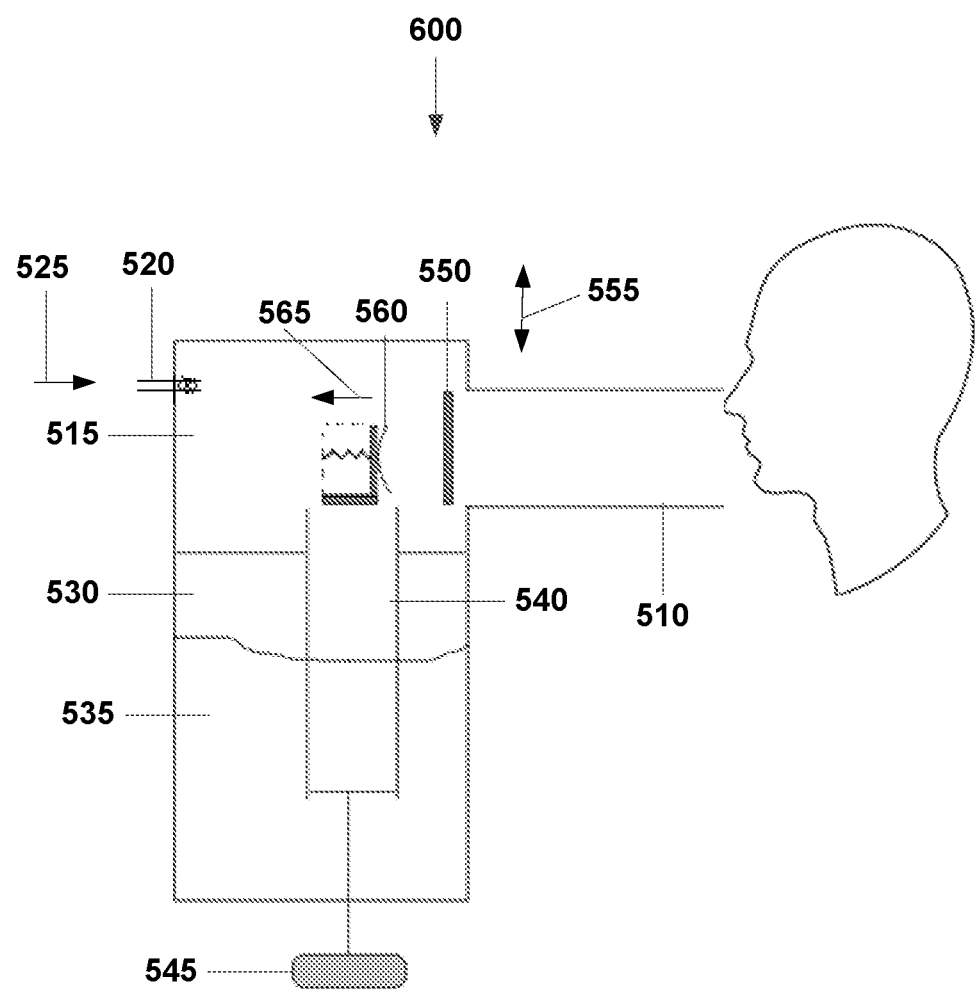
FIG. 6 shows an exemplary mechanical delivery apparatus according to embodiments of the present invention.

FIG. 6 shows an exemplary mechanical delivery apparatus 600 according to embodiments of the present invention comprising: a medicine compartment 530 storing medicine powder (drug) 535, an upper compartment 515, a spout 510 connected to the upper compartment 515, a unidirectional valve 520 which enables airflow in the direction of arrow 525, a release mechanism implemented by a mechanical component 540 and a knob 545 configured to transfer medicine from the medicine compartment 530 to the upper compartment 515 and to enable opening of the valve\shutter. The apparatus also comprises a shutter 550 configured to enable\disable the path between the spout 510 and the upper compartment 515 (by moving in the direction of the dual head arrow 555) and a test mechanism implemented by an accurate micro mechanic element (MME) 560. The MME is sensitive to the airflow exhaled by the patient and is pushed back, in the direction of arrow 565, by the patient's exhalation. The full operation is explained below in conjunction with FIG. 7. The test mechanism in this embodiment does not provide test results but leaves the personalized medicine dosage in the upper compartment according to the patient's airflow.

According to embodiments of the invention, in a case where the operation is performed manually by the patient, a controller is not needed. In a case where at least part of the process is performed automatically, the apparatus further comprises a controller and an actuator.

According to embodiments of the invention, the medicine compartment 530 may be a replaceable compartment.

Figure 7:
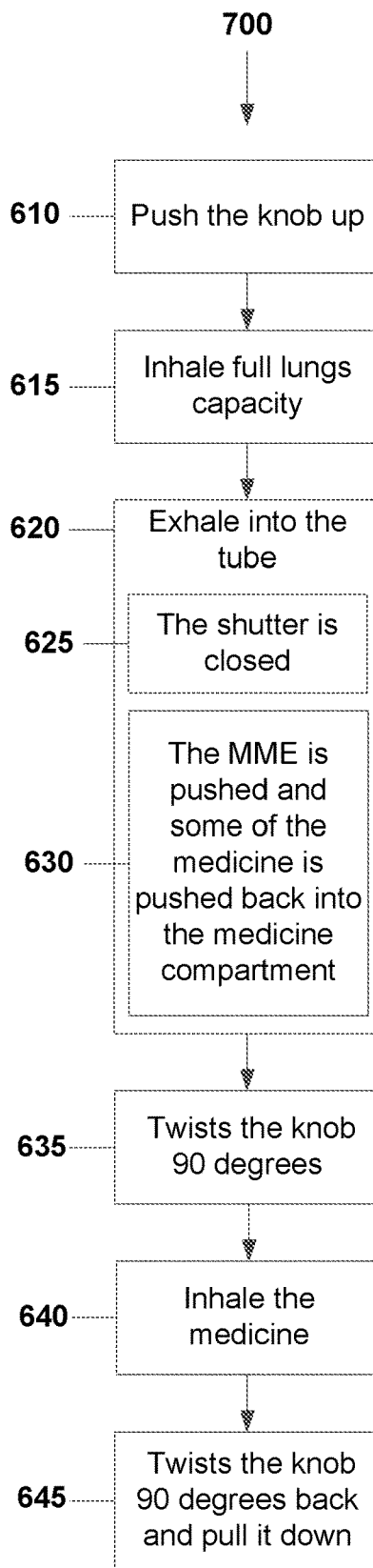
FIG. 7 is a flowchart showing the process performed by a patient who uses the delivery apparatus of FIG. 6.

FIG. 7 is a flowchart 700 showing the process performed by a patient who uses the delivery apparatus 600 of FIG. 6. At the beginning of the process the knob 545 is mounted at the bottom of the mechanical component 540 and the shutter 550 is open (namely, the path between the spout 510 and the upper compartment 515 is open). In step 610, the patient pushes the knob up. By doing that, the maximum medicine dosage is delivered from the medicine compartment 530 to the upper compartment 515. In step 615, the patient inhales full lungs capacity (not through the apparatus) and in step 620, he exhales into the spout 510. In step 625, after a predefined period of time (e.g. 1 sec) the shutter 550 closes the path between the spout 510 and the upper compartment 515. In step 630, as a result of the patient's exhalation, the MME is pushed and some of the medicine is pushed back into the medicine compartment 530 (in proportion to the exhaled airflow according to the FEV1\quantity calibration function). This process adjusts the medicine dosage personally to each patient. In step 635, the patient twists the knob (e.g. 90 degrees) in order to open the shutter. In step 640, the patient inhales the medicine. In step 645, the patient turns the knob (e.g. 90 degrees back) and pulls it back down.

Figure 8:
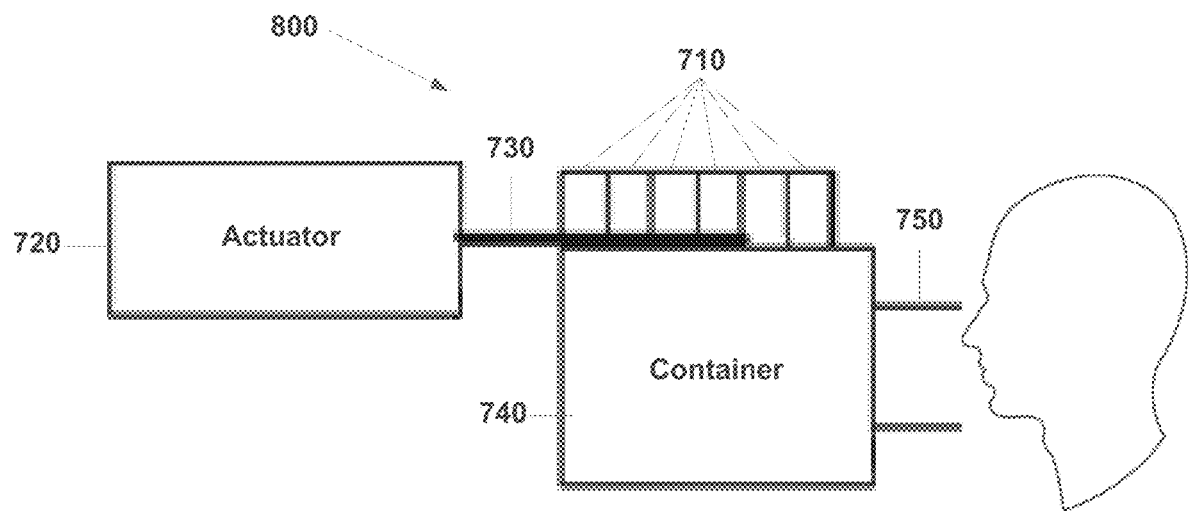
FIG. 8 demonstrates another personalized drug dosage release mechanism apparatus according to embodiments of the present invention.

FIG. 8 demonstrates another personalized drug dosage release mechanism (104 of FIG. 1) 800. According to embodiments of the present invention, the dosage determination mechanism and process may be one of the dosage determination mechanisms and processes that were described above in conjunction with FIGS. 2 and 4. The medicine powder (drug) is contained inside individual powder cells 710. After the dosage has been determined, the release mechanism implemented by an actuator 720 (e.g. motor) pulls a disk 730 which opens a number of powder cells that will result in the right dosage of powder to be released into the container (intermediate compartment) 740 for the patient to inhale via the spout 750 (101 of FIG. 1).

Figure 9:
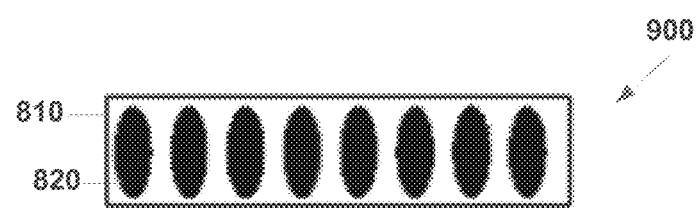
FIG. 9 demonstrates another personalized drug dosage release mechanism according to embodiments of the present invention.

FIG. 9 demonstrates another personalized drug dosage release mechanism 900 (104 of FIG. 1). According to embodiments of the invention, the strip 810 (which may be part of a roll) is coated on one side with dry powder (drug) 820. After the medicine dosage has been determined by one of the dosage determination mechanisms and processes that were described above in conjunction with FIGS. 2 and 4, the medicine powder 820 is peeled off the strip 810 accordingly (by a peeling mechanism—not shown).

Each peeled distance equals a certain amount of powder (peeled volume).

According to embodiments of the present invention, the opposite side of the strip may be used as a test mechanism. A chemical agent may determine parameters involved in the FEV1 test. The apparatus may have a color chart correlated to FEV1 results, namely, each color indicates a different dosage. By analyzing the color (e.g. by a camera and image processing) the apparatus may determine the right dosage.

Figure 10:
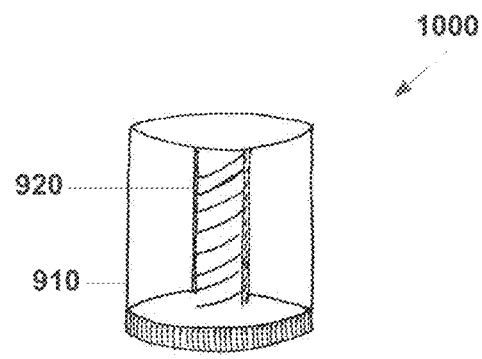
FIG. 10 demonstrates another personalized drug dosage release mechanism according to embodiments of the present invention.

FIG. 10 demonstrates another personalized drug dosage release mechanism 1000 (104 of FIG. 1). According to embodiments of the present invention, after the medicine dosage has been determined by one of the dosage determination mechanisms and processes that were described above in conjunction with FIGS. 2 and 4, the personalized dosage may be delivered from the medicine compartment 910 to the patient by a spiral or a screw 920. The spiral (or the screw) has circumferential slots thus when it rotates medicine fills the slots and is delivered to an intermediate compartment or to the Inhale\exhale spout (not shown) for the patient to inhale. The dosage is controlled by controlling the rotation of the spiral\screw.

Figure 11A:
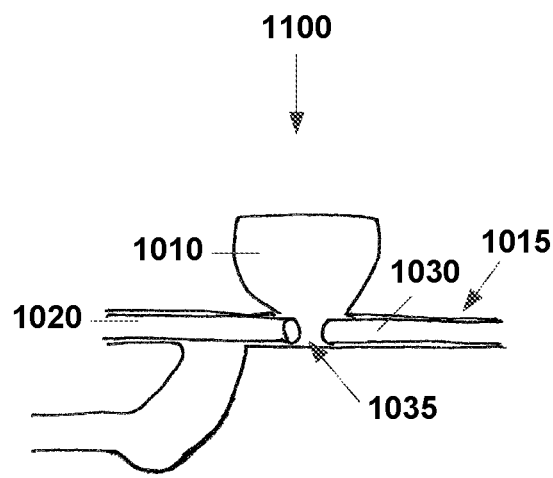
FIGS. 11A and 11B demonstrate another personalized drug dosage release mechanism according to embodiments of the present invention.
Figure 11B:
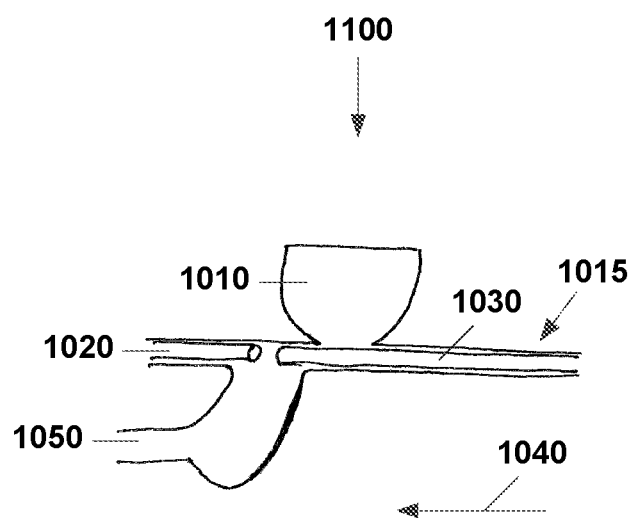

FIGS. 11A and 11B demonstrate another personalized drug dosage release mechanism 1100 (104 of FIG. 1). According to embodiments of the present invention, the medicine may be delivered from the medicine compartment 1010 to the patient through a channel 1015 having two movable parts 1020 and 1030 (e.g. cylinders). After the medicine dosage has been determined by one of the dosage determination mechanisms and processes that were described above in conjunction with FIGS. 2 and 4, the gap 1035 between the parts is determined accordingly and placed under the medicine compartment 1010. When the medicine fills the gap, the parts 1020 and 1030 move together in the direction of arrow 1040 and the medicine is delivered to an intermediate compartment or to the Inhale\exhale spout (not shown) through pipe 1050.

Figure 12A:
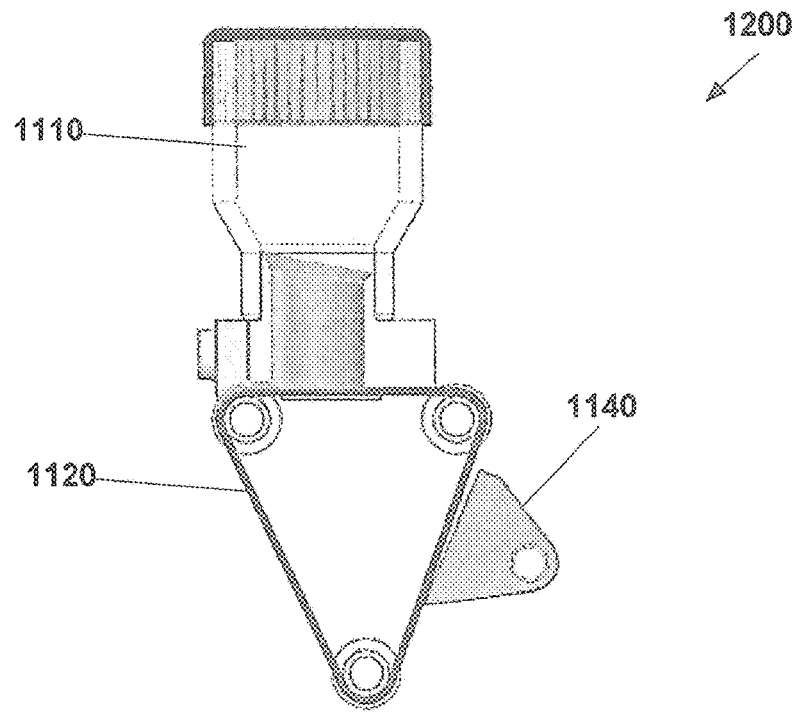
FIGS. 12A and 12B demonstrate another personalized drug dosage release mechanism according to embodiments of the present invention.
Figure 12B:
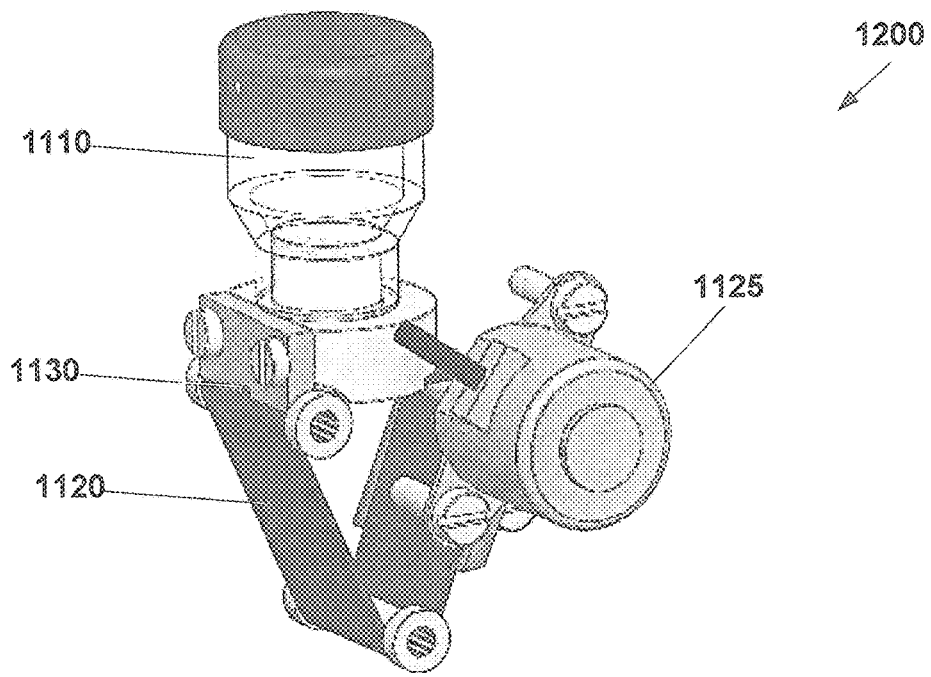

FIGS. 12A and 12B demonstrate another personalized drug dosage release mechanism 1200 (104 of FIG. 1). According to embodiments of the present invention, a medicine compartment 1110 is placed above a conveyor 1120. The medicine (drug) from the compartment lays on the conveyor. After the medicine dosage has been determined by one of the dosage determination mechanisms and processes that were described above in conjunction with FIGS. 2 and 4, the conveyor progresses via an actuator 1125 (e.g. stepper motor) and the determined amount of the medicine is released through the orifice 1130 into an intermediate compartment (not shown) for the patient to inhale. The apparatus that uses this mechanism is configured to determine the conveyor's progression rate in accordance with the determined medicine dosage. Part 1140 may be configured to clean the remnants of the medicine from the conveyor 1120. According to embodiments of the invention, the orifice 1130 may be a fixed size orifice. Alternatively, the apparatus may be configured to control the orifice's size in order to assist in faster medicine release.

According to embodiments of the invention, the conveyor 1120 may be grooved, namely, it may have grooves configured to be filled with medicine. When the conveyor progresses, the grooves pass beneath the medicine compartment and are filled with medicine. The apparatus that uses this mechanism is configured to determine the conveyor's progression rate in accordance with the determined medicine dosage in order to release the right number of grooves.

FIG. 13 is a schematic view of another exemplary drug delivery apparatus 1300 according to embodiments of the present invention. In order to inhale a personalized medicine dosage, a patient may input his personal details to the apparatus via a user interface such as a touch screen for example (not shown) and place a medicine capsule in the designated location 1205. The details may be age, weight, height, sex, etc. Then, the patient inhales full lungs capacity (not through the apparatus), places his mouth on the spout 1210 and exhales. The exhaled air flows through the tube 1220 and is measured twice by a test mechanism, once by a sensor 1230 mounted in the widest part of a venturi nozzle 1250 and a second time by a sensor 1240 mounted in the narrowest part of the nozzle 1250. The difference between the measurements is translated into a volumetric flow rate according to which the controller (not shown) determines the personalized dosage of medicine to release. The determined dosage may be released by one of the release mechanisms describe above in conjunction with FIGS. 8 through 12B (For example the mechanism of FIGS. 12A and 12B is shown). The medicine dosage is released to the bottom of the funnel 1255 (top of part 1270).

FIG. 13A describes the inhalation stage of the process described in conjunction with the apparatus of FIG. 13. According to embodiments of the invention, in order to inhale the medicine, the patient pushes the spout 1210 in the direction of arrow 1260. As a result of this action, the part 1270 connected to the tube 1220, moves in the same direction, the medicine dosage is released from the bottom of the funnel 1255 into the tube 1220 and the patient may inhale it. Spring 1280 which has been pressed when to patient pushed the spout 1210 is configured to return the spout to its original position (in the direction of arrow 1290).

According to embodiments of the invention, as depicted in FIG. 13B, an opposite slant part 1270A may be mounted in the upper left side of part 1270 in order to assist the medicine dosage to be released into the tube 1220 (not shown) and\or clean remnants.

Figure 14:
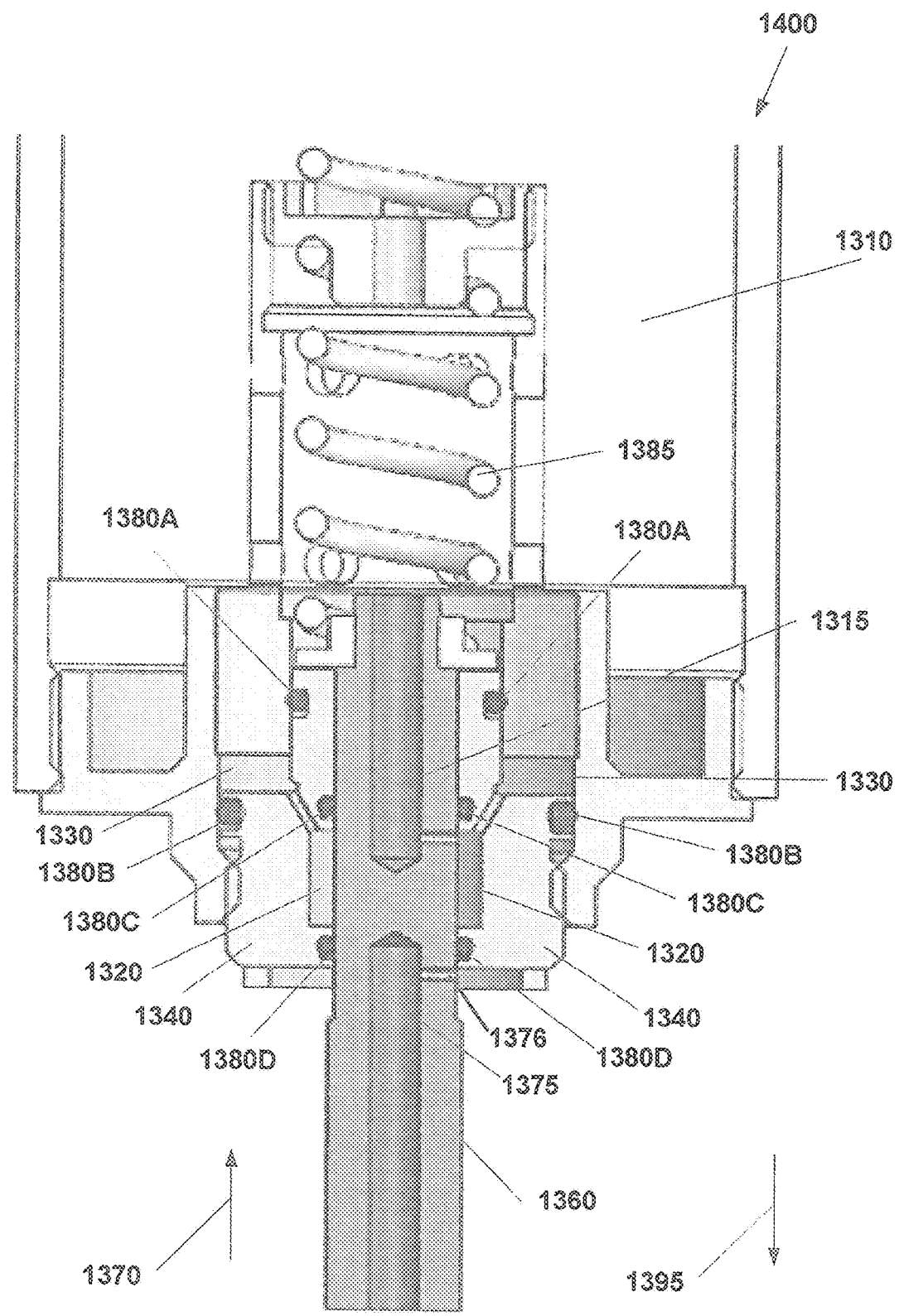
FIGS. 14 and 14A demonstrate another personalized drug dosage release mechanism according to embodiments of the present invention.
Figure 14A:
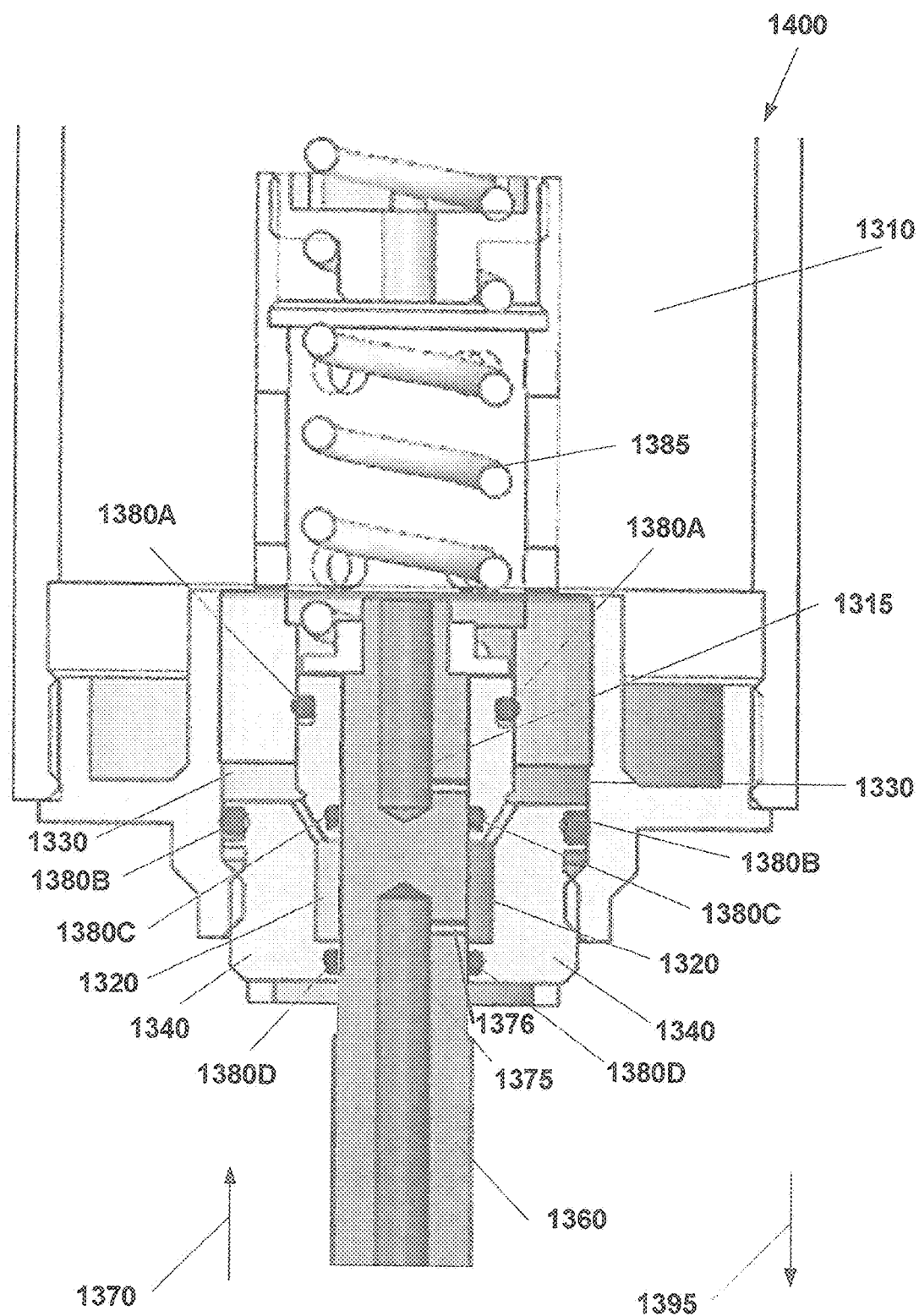

FIGS. 14 and 14A demonstrate another personalized drug dosage release mechanism (104 of FIG. 1). According to embodiments of the present invention, the medicine (pressurized fluid) contained in the compartment 1310, passes through a nozzle 1315 and fills a fixed size circumferential cavity 1320 and an adjustable circumferential cavity 1330. The size of the adjustable circumferential cavity 1330 may be determined according to the dosage determination mechanisms and processes that were described above in conjunction with FIGS. 2 and 4. The adjustable circumferential cavity 1330 size's adjustment may be done manually by, for example, instructing the patient to manually rotate part 1340 (which rotates around part 1360) which changes the cavity's size or automatically by an actuator (not shown) configured to do so (for example). When part 1340 rotates to a predefined direction, it enlarges the cavity 1330 volume and when it rotates to the other direction, it minimizes the cavity 1330 volume. The cavities 1320 and 1330 are connected to each other and a pressure inside the medicine compartment ensures filling them. In order to inhale the medicine (FIG. 14A) the patient pushes part 1360 in the direction of arrow 1370, the upper side of the nozzle 1375 (hole 1376) reaches the cavity 1320 (FIG. 14A) and the medicine is released through a spout (not shown) connected to the nozzle 1375. Seals 1380A-1380D are mounted as depicted in the figures and are configured to prevent medicine leakage. Spring 1385 which has been pressed when the patient pushed the part 1360 is configured to return the nozzle 1375 to its original position (in the direction of arrow 1395).

According to embodiments of the invention, the nozzle may be fixed to the apparatus's cover and the medicine compartment may be pressed by the patient against it in order to release the medicine.

Figure 14B:
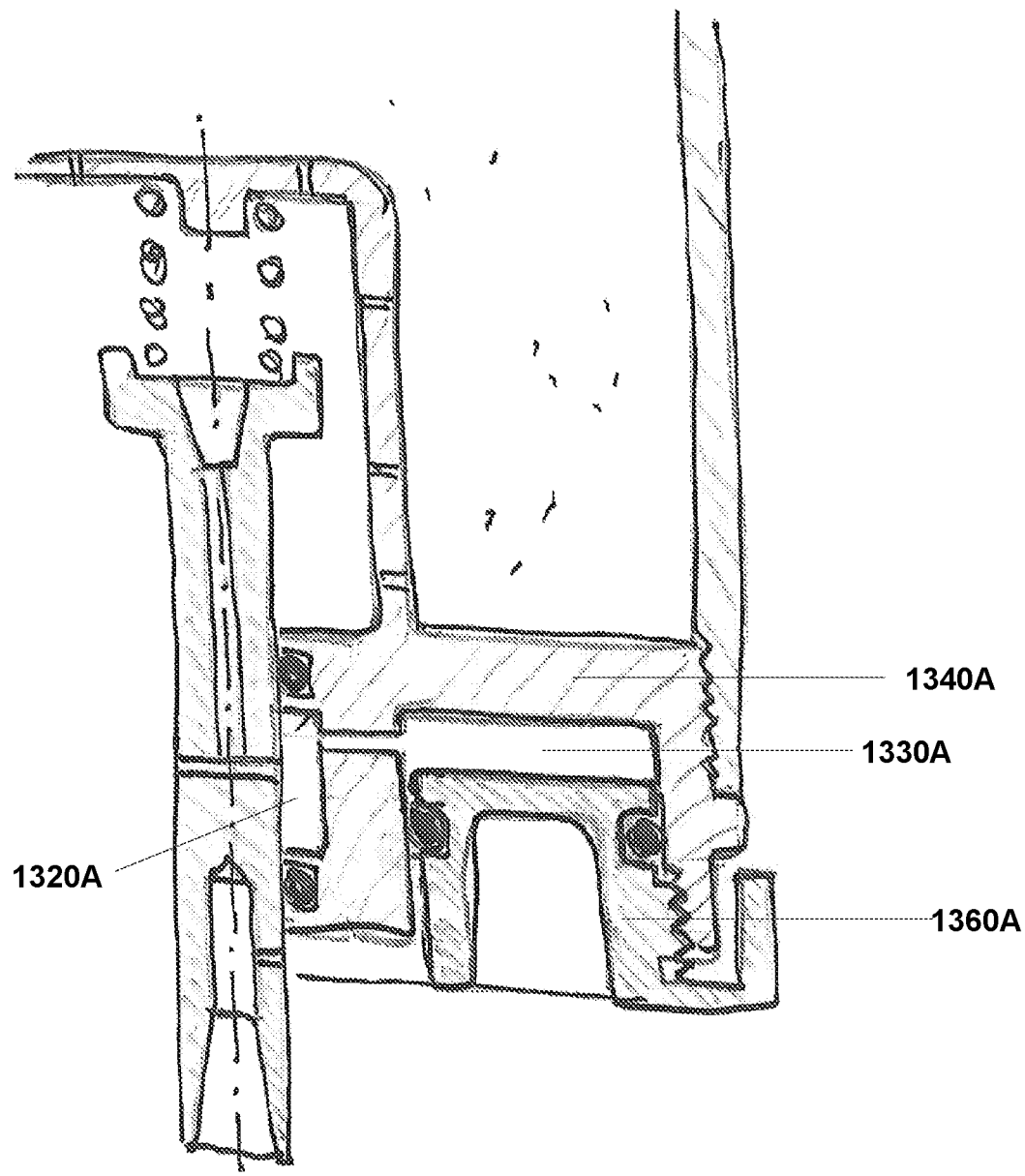
FIG. 14B demonstrates a similar personalized drug dosage release mechanism to the one described in conjunction with FIGS. 14 and 14A, except the adjustable cavity.

FIG. 14B demonstrates a similar personalized drug dosage release mechanism (104 of FIG. 1) to the one described in conjunction with FIGS. 14 and 14A, except the adjustable cavity 1330A. According to embodiments of the present invention, the adjustable cavity 1330A is mounted between the parts 1340A and 1360A and is connected to the fixed size cavity 1320A. The adjustable cavity 1330A may be circumferential or not. If it is not, at least one cavity 1330A may be placed on the circumference of the apparatus and is (are) connected to the fixed size cavity 1320A. By screwing the part 1360A in a predetermined direction, the cavity's volume increases. The screwing may be done manually by the patient or automatically by an actuator according to the determined personalized drug dosage. If the adjustable cavity 1330A is circumferential, the size determination mechanism is similar to the one described in conjunction with FIGS. 14-14A.

Figure 15:
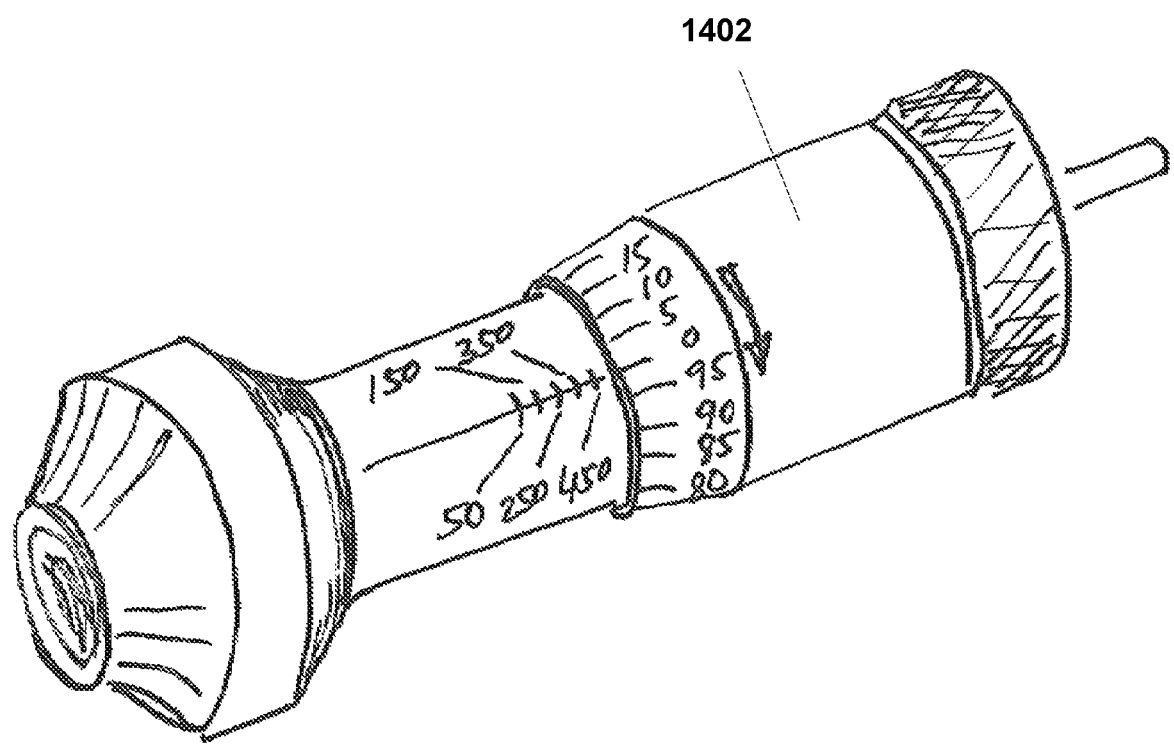
FIG. 15 demonstrates an outer view of an exemplary manual mechanism which enables to determine the drug dosage.

FIG. 15 demonstrates an outer view of an exemplary manual mechanism which enables to determine the drug dosage. The mechanism may be configured to adjust the size of the adjustable cavities (1330 or 1330A) that were described in conjunction with FIG. 14 through 14B (the circumferential cavities embodiments). Part 1402 rotates parts 1340 or 1360A according to the embodiment which determine the adjustable cavity's size (volume).

Figure 16:
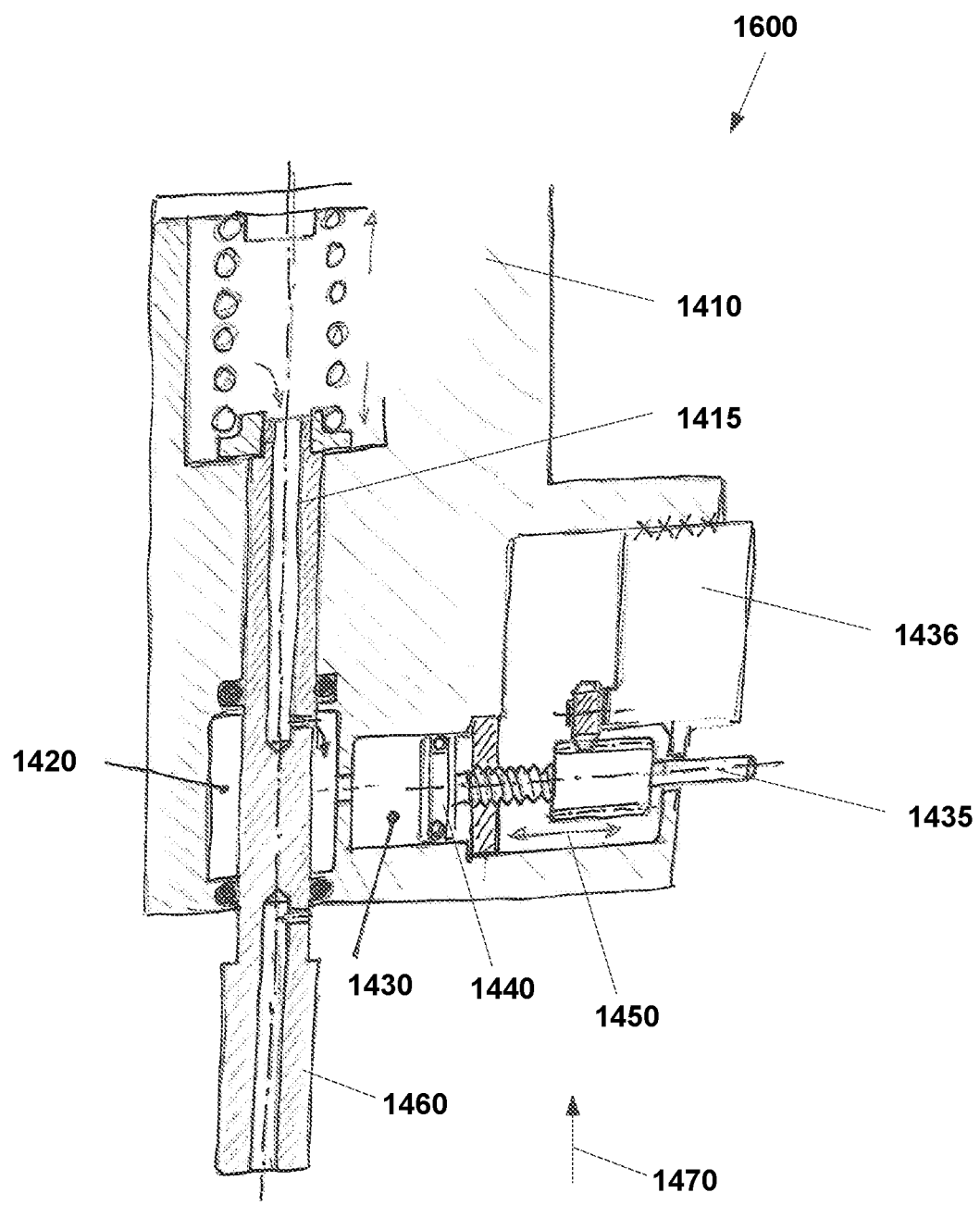
FIGS. 16 and 16A demonstrates another personalized drug dosage release mechanism according to embodiments of the present invention.
Figure 16A:
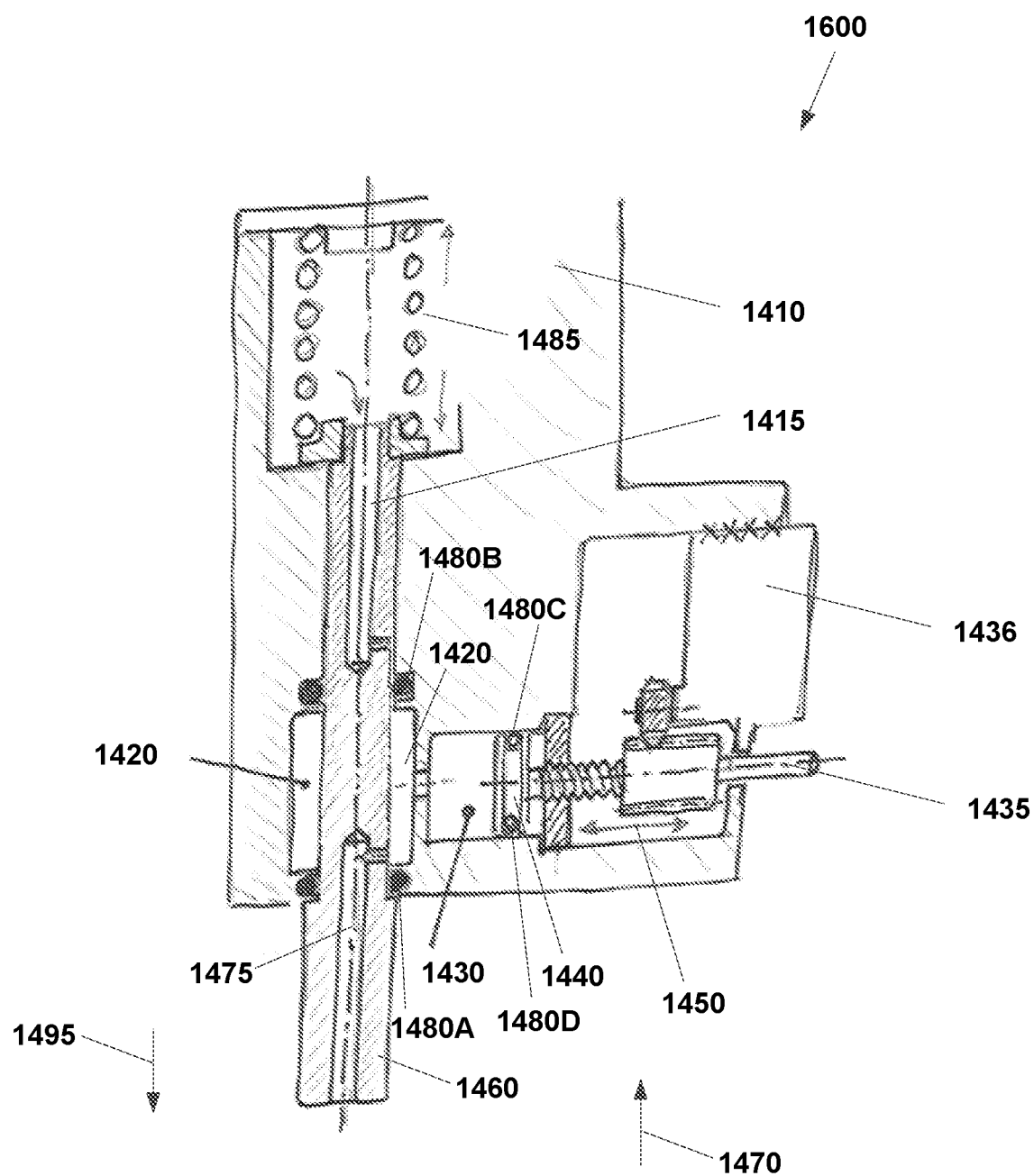

FIGS. 16 and 16A demonstrate another personalized drug dosage release mechanism (104 of FIG. 1) 1600. According to embodiments of the present invention, the medicine (pressurized fluid) contained in the compartment 1410, passes through the nozzle 1415 and fills a fixed size circumferential cavity 1420 and an adjustable cavity 1430. The cavities 1420 and 1430 are connected to each other and a pressure inside the medicine compartment ensures filling them. The size of the adjustable cavity 1430 is determined according to one of the dosage determination mechanisms and processes that were described above in conjunction with FIGS. 2 and 4. The size adjustment may be done manually by, for example, instructing a patient to rotate a screw(s) 1435 which changes the cavity's size (e.g. by the manual mechanism of FIG. 15) or automatically by an actuator 1436 configured to do so. The screw(s) or the actuator moves part 1440 in the directions of the dual head arrow 1450 according to the determined dosage. In order to inhale the medicine the patient pushes part 1460 in the direction of arrow 1470, the upper side of the nozzle 1475 reaches the cavity 1420 (FIG. 16A) and the medicine is released through a spout (not shown) connected to the nozzle 1475. The Seals 1480A-1480D are mounted as depicted in the figures and configured to prevent medicine leakage. Spring 1485 is configured to return the nozzle 1475 to its original position (in the direction of arrow 1495).

According to embodiments of the invention, the nozzle may be fixed to the apparatus's cover and the medicine compartment may be pressed by the patient against it in order to release the medicine.

Figure 17A:
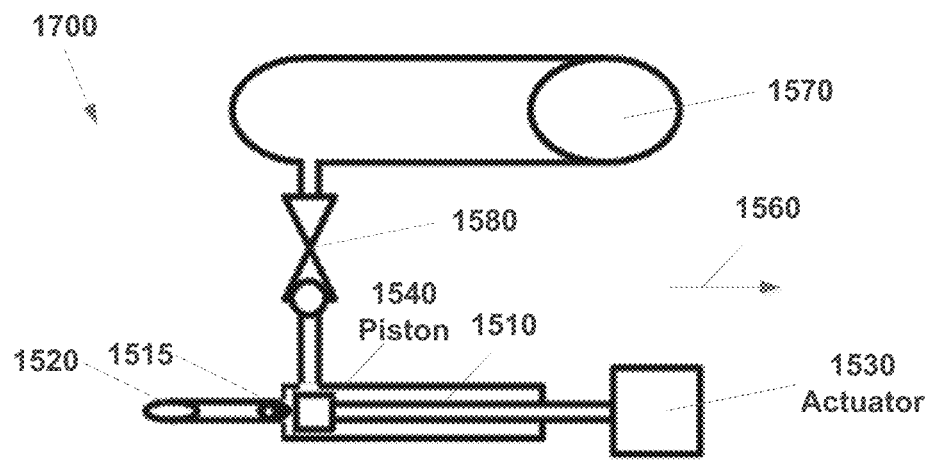
FIGS. 17A through 17C demonstrate another personalized drug dosage release mechanism according to embodiments of the present invention.
Figure 17B:
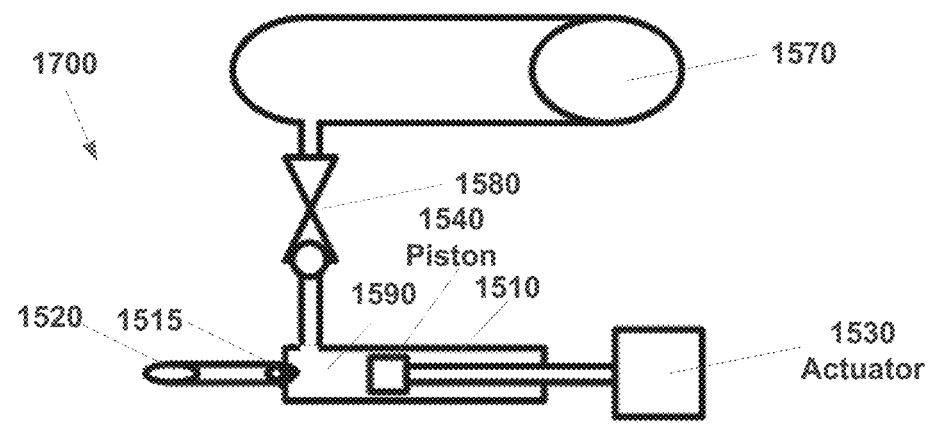
Figure 17C:
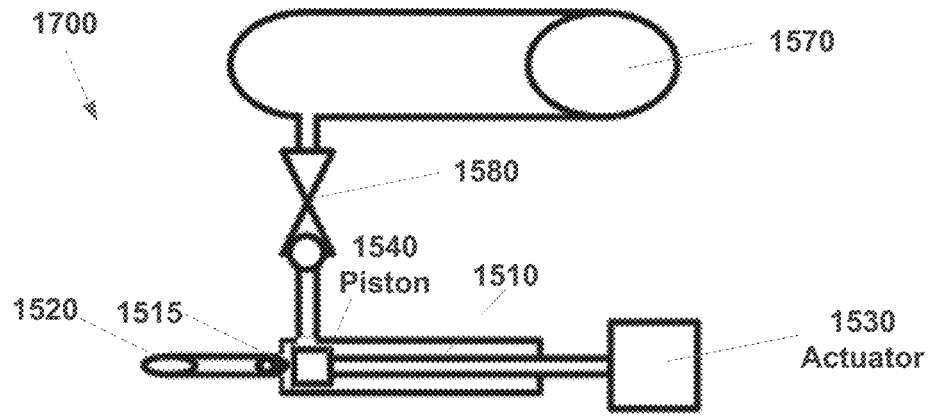

FIGS. 17A through 17C demonstrate another personalized drug dosage release mechanism (104 of FIG. 1) 1700. According to embodiments of the present invention, the dosage determination mechanism and process may be one of the dosage determination mechanisms and processes that were described above in conjunction with FIGS. 2 and 4. According to the determined dosage, an actuator 1530 pulls a piston 1540 in the direction of arrow 1560. As a result of this action, a medicine from a medicine compartment 1570 is sucked through a unidirectional valve 1580 and fills the created cavity 1590 (FIG. 17B). A unidirectional valve 1515 seals a nozzle 1520 in order to enable the suction from the medicine compartment. When the dosage is ready, the apparatus which uses this release mechanism may instruct the patient to place his mouth on a spout (not shown) connected to the nozzle 1520, press a button (for example) and inhale the medicine released by the actuator 1530 (FIG. 17C).

Figures 18, 18A:
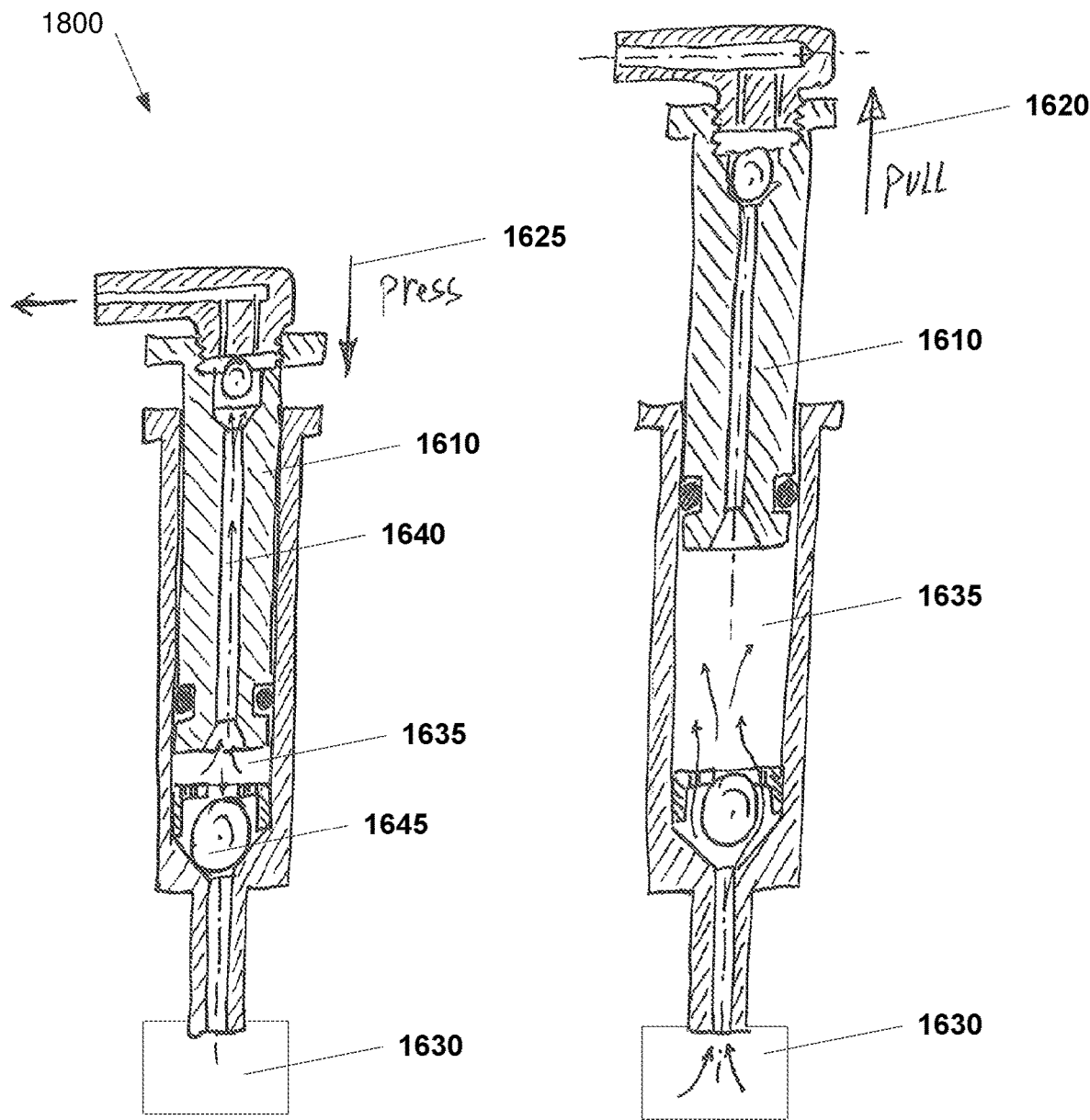
FIGS. 18 and 18A demonstrate another personalized drug dosage release mechanism according to embodiments of the present invention.

FIGS. 18 and 18A demonstrate another personalized drug dosage release mechanism (104 of FIG. 1) 1800. According to embodiments of the present invention, the dosage determination mechanism and process may be one of the dosage determination mechanisms and processes that were described above in conjunction with FIGS. 2 and 4. According to the determined dosage, part 1610 is pulled by the patient in the direction of arrow 1620 and sucks medicine (pressurized fluid) from the medicine compartment 1630 into an intermediate compartment 1635. In order to inhale the medicine, the patient pushes the part 1610 (FIG. 18A) in the direction of arrow 1625, a small sphere 1645 seals the connection between the intermediate compartment 1635 and the medicine compartment 1630 and the medicine flows in the direction of arrow 1620 through the nozzle 1640 mounted inside the part 1610. The nozzle is connected to a spout (not shown) for the patient to inhale.

According to embodiments of the invention, the medicine compartment 1630 may be a replaceable medicine compartment or a fixed medicine compartment.

According to embodiments of the invention, the medicine in some of the embodiments described above is released from the medicine compartment to an intermediate compartment (the personalized dosage compartment) in a constant flow rate (according to the medicine compartment's pressure). In order to maintain this flow rate while enlarging the intermediate compartment, the present invention offers to control the nozzle's flow rate.

Figure 19:
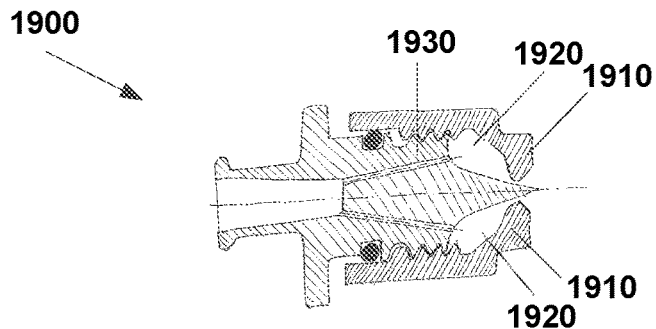
FIG. 19 demonstrates a solution to the intermediate compartment pressure regulation.

FIG. 19 demonstrates a solution to the intermediate compartment pressure regulation—a nozzle 1900 which may be mounted in or at the spout's end of any one of the nozzles described above in conjunction with FIGS. 14, 14A, 14B and 16 through 18A. According to the determined medicine dosage, the intermediate compartment's size is changed or being changed. While enlarging the compartment's size, the pressure of the content in the compartment decreases. In order to release the medicine from this compartment for the patient to inhale in the original pressure (or at least close to the original pressure), the apparatus which uses the nozzle 1900 may adjust the nozzle's flow rate. The nozzle 1900 adjustment may be done by rotating a nut 1910 which increases or decreases the cavity's 1920 volume created between the nozzle head 1930 and the nut 1910. By rotating the nut in a predetermined direction, the cavity's volume increases thus lower pressure is created. By rotating the nut to the other direction, the cavity's volume decreases thus a higher pressure is created. The nut may rotate by an actuator (not shown) controlled by a controller (not shown) which determines the rotation according to the intermediate compartment's size.

The actuators described hereinabove may be DC Motor, servo motor, stepper motor, PZT, shape memory alloy (SMA), pneumatic actuator, hands power, magnetic actuator, magnetostrictive actuator, solenoid, thermal actuator or any other actuator known in the art and suitable for the task.

Figure 20:
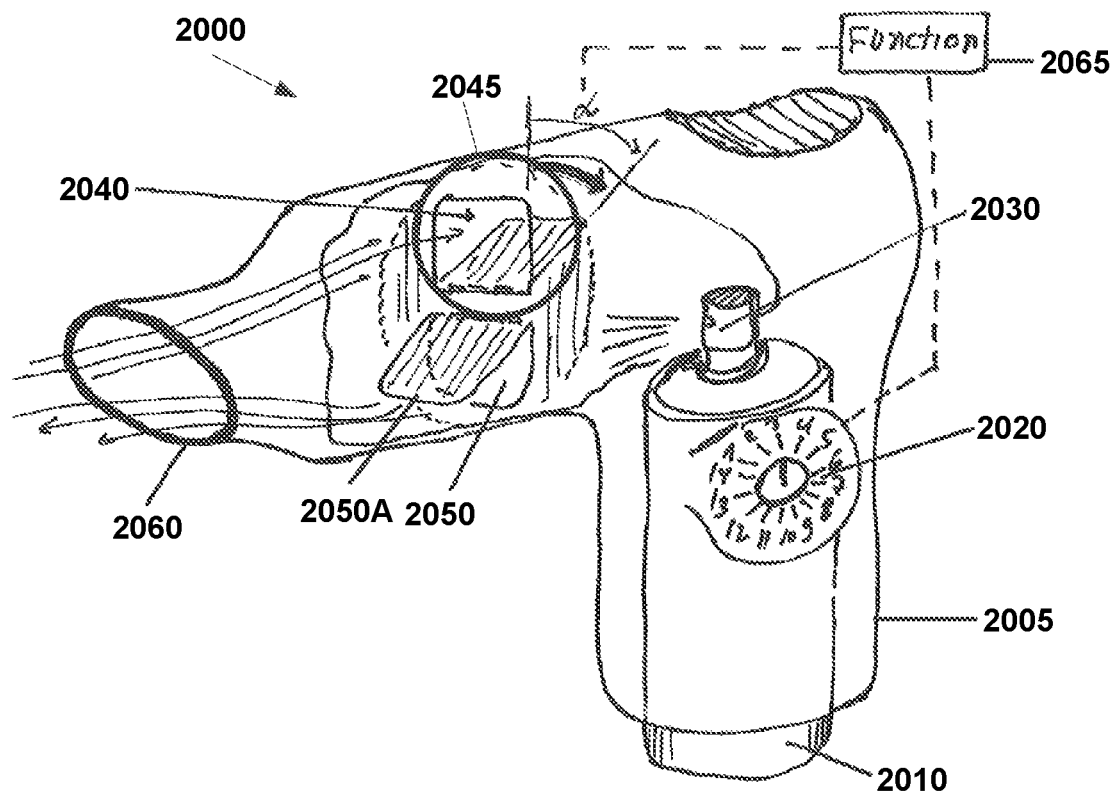
FIG. 20 is a schematic view of another exemplary mechanical delivery apparatus according to embodiments of the present invention.

FIG. 20 is a schematic view of another exemplary mechanical delivery apparatus 2000 according to embodiments of the present invention comprising, a housing 2005 comprising a medicine compartment 2010 storing medicine (pressurized fluid—not shown), dosage setting dial 2020, nozzle 2030, a test mechanism 2040, a release mechanism 2050, a transparent window (not shown) mounted in front of the test mechanism 2040 and a spout 2060. The function 2065 represents the correlation between the angle alpha and the dosage setting dial 2020. Air flow can pass from the spout 2060 side to the nozzle 2030 only through the test mechanism 2040. Medicine can pass from the nozzle 2030 to the spout 2060 only through the release mechanism 2050.

Figure 20A:
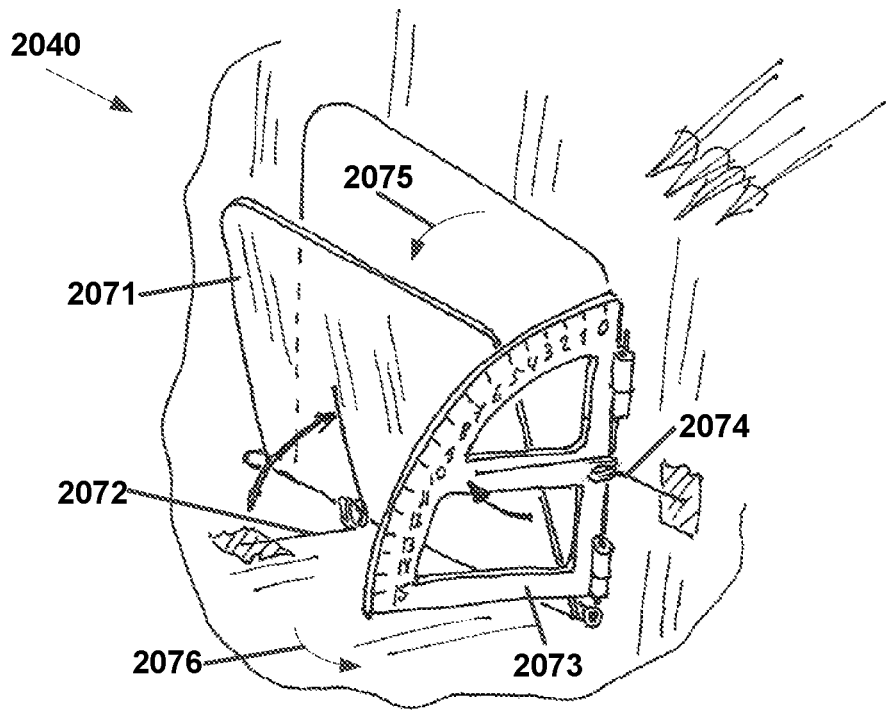
FIG. 20A shows an enlargement of detail 2045 of FIG. 20.

FIG. 20A shows an enlargement of detail 2045 of FIG. 20 which comprises the test mechanism 2040. The test mechanism 2040 comprises a flap 2071, a spring 2072 connected to the flap 2071 on one side and to a fixed location on its other side, and a side flap 2073 pressed against the flap 2071 by a spring 2074 which is connected to the side flap 2073 on one side and to a fixed location on its other side.

In operation, referring to both FIGS. 20 and 20A, a patient inhales full lungs capacity (not through the apparatus) and exhales into the apparatus through the spout 2060. The air flow pushes the flap 2071 in the direction of arrow 2075. The side flap 2073 which is pressed against the flap 2071 is pushed by the flap 2071 in the direction of arrow 2076. The spring's 2074 pressure keeps the flap 2071 in its position (e.g. on number 5 as shown in FIG. 20A) long enough for the patient to see through the transparent window (not shown) the dosage he needs to adjust. The patient sets the dosage setting dial 2020 accordingly and pushes the medicine compartment 2010 against the apparatus's housing 2005. When the compartment is pushed, medicine is released through the nozzle 2030. When the patient inhales trough the spout 2060, the release mechanism's flap 2050A is opened by the force of the patient's suction and the medicine is released.

According to embodiments of the present invention, the test and/or the release mechanisms may be implemented by a mechanical mechanism comprising, a propeller configured to rotate when a patient blows toward it. While rotating, the propeller may actuate any of the release mechanisms described above in conjunction with FIGS. 8-14B and 16-18A. The actuation may be done directly by the propeller. Alternatively, the propeller may load an actuator which may be configured to actuate any of the release mechanisms described above in conjunction with FIGS. 8-14B and 16-18A.

Figure 21:
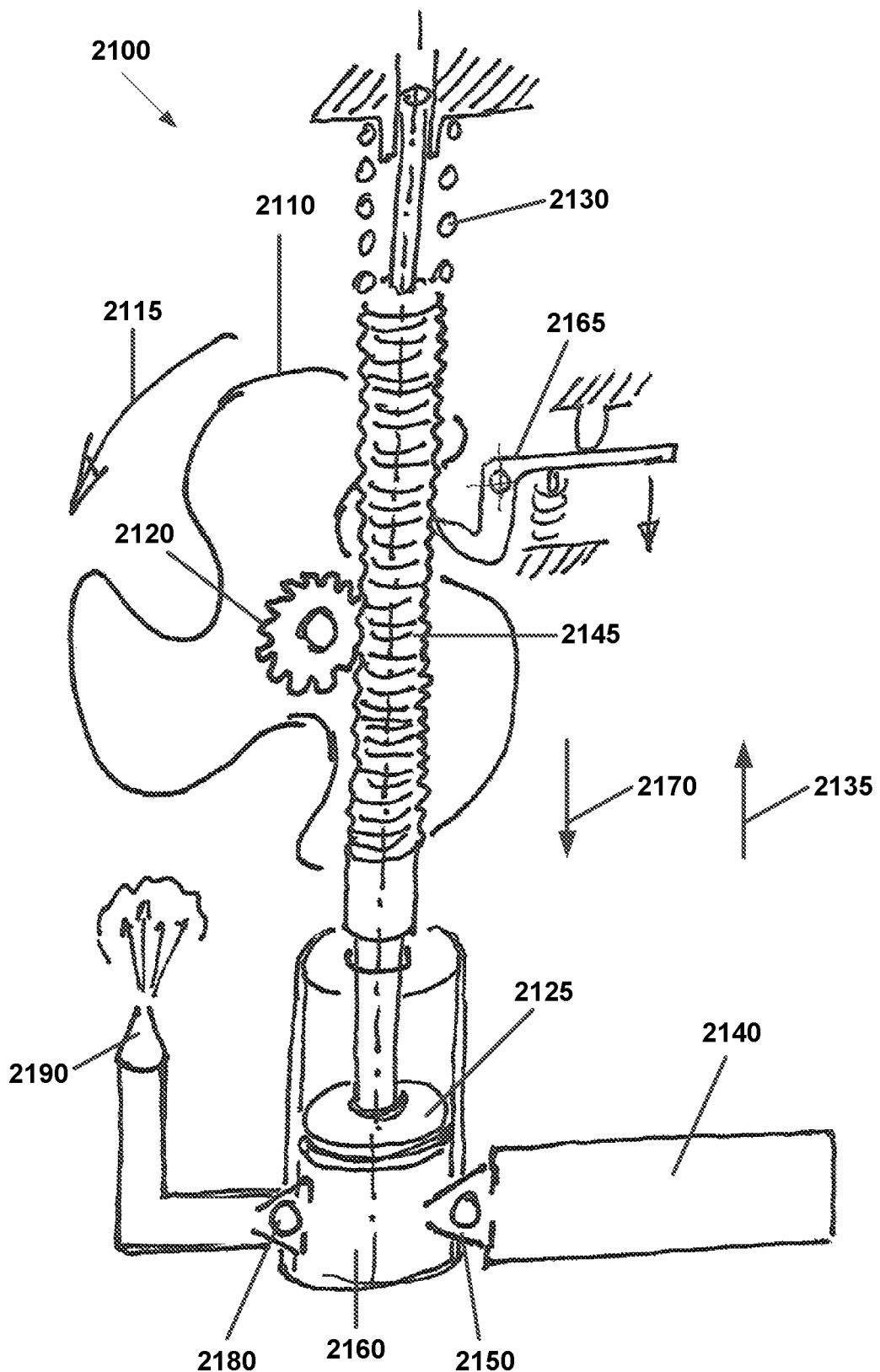
FIG. 21 demonstrates an exemplary mechanical mechanism according to embodiments of the invention.

FIG. 21 demonstrates an exemplary mechanical mechanism 2100 according to embodiments of the invention. The test mechanism in this embodiment is implemented by a propeller 2110. When a patient blows a full-lung exhalation through a spout (not shown) towards the propeller 2110, the propeller rotates in the direction of arrow 2115 according to the patient's air flow. A cog-wheel 2120 mounted in the center of the propeller 2110 and connected with a grooved pole 2145 connected to a piston 2125, lifts the piston 2125 in the direction of arrow 2135 and loads a spring 2130. While the piston is lifted, it sucks drug from a drug compartment 2140, through a unidirectional valve 2150, into an intermediate compartment 2160. The left side of part 2165 prevents the return of the piston 2125. In order to inhale the drug, the patient presses on the right side of part 2165 and releases the loaded spring which pushes the piston 2125 back in the direction of arrow 2170. The piston forces the drug out from the intermediate compartment 2160, through a unidirectional valve 2180, to spout 2190 for the patient to inhale.

Alternatively, the propeller may be configured to pull the disk which opens the right number of drug cells (FIG. 8), actuate the peeler of FIG. 9, rotate the spiral of FIG. 10, determine the distance between the two movable parts of FIG. 11A and move them, actuate the conveyor of FIG. 12A, enlarge the size (volume) of the adjustable cavities of FIGS. 14-14B and 16-16A, etc.

Figure 22:
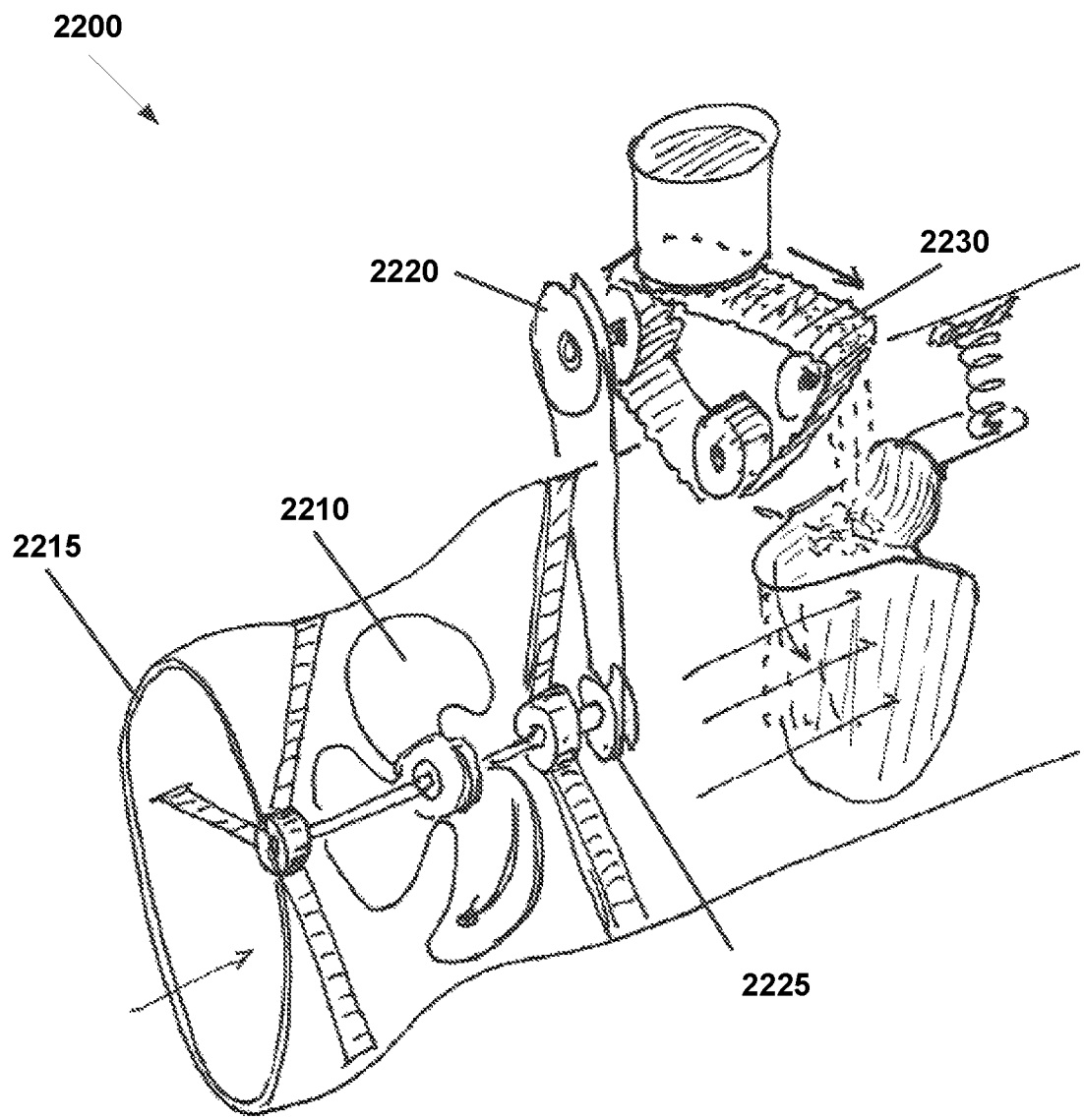
FIG. 22 demonstrates another exemplary mechanical mechanism 2200 according to embodiments of the invention.

FIG. 22 demonstrates another exemplary mechanical mechanism 2200 according to embodiments of the invention. The test mechanism in this embodiment is implemented by a propeller 2210. When a patient blows a full-lung exhalation through a spout 2215 towards the propeller 2210, the propeller rotates according to the patient's air flow and rotates a pulley 2220 (directly or via at least one other pulley such as pulley 2225). The pulley 2220 is connected to a conveyor 2230 which releases the drug according to the propeller rotation. The conveyor and the releasing method may be similar to the one described above in conjunction with FIGS. 12A-12B.

According to embodiments of the invention, the medicine compartment of the delivery apparatuses that were described above may be replaceable, e.g. a capsule containing the medicine. The capsule may have for example an aluminum bottom that is breached (e.g. by a needle) when the capsule is placed in the apparatus.

According to embodiments of the invention, the delivery apparatuses that were described above may also comprise a cover, such as plastic cover, configured to cover the exhale\inhale spout or nozzle.

It will be appreciated by persons skilled in the art that the present invention is not limited to what has been particularly shown and described hereinabove. Rather the scope of the present invention is defined by the appended claims and includes combinations and sub-combinations of the various features described hereinabove as well as variations and modifications thereof which would occur to persons skilled in the art upon reading the foregoing description.

The invention claimed is:

1. An adaptive personalized drug delivery apparatus configured to perform a spirometry test, determine a personalized drug dosage according to said test and enable inhalation of said personalized drug dosage, comprising:
    drug containing means;
    a spout configured to receive full lung exhalation of a user;
    a first tube connected with a second tube and a third tube through a valve defining a drug release mechanism;
    wherein said second tube is connected with said drug containing means; said third tube is connected with said spout; thereby said drug containing means being connected with said spout via said valve;
    a test mechanism comprising a sensor configured to perform said spirometry test by measuring said exhalation;
    an actuator configured to move said valve; and
    a controller connected with said test mechanism and said release mechanism;
    said controller configured to determine a personalized drug dosage according to said measured exhalation; actuate said actuator to direct said valve to open a path between said drug containing means and said spout, through said second tube said valve and said third tube, thereby enabling said user to inhale said determined personalized drug dosage; and redirect said valve to close said path between said drug containing means and said spout according to said determined personalized drug dosage and connect a path between said third tube and said first tube, stopping medicine flow from said drug containing means and re-enabling exhalation.

2. The personalized drug delivery apparatus of claim 1, wherein said drug containing means comprise one of compartment, individual cells and strip.

3. The personalized drug delivery apparatus of claim 1, wherein said drug containing means is replaceable.

4. The personalized drug delivery apparatus of claim 3, wherein said replaceable drug containing means is a capsule.

5. A method of performing a spirometry test, determining a personalized drug dosage according to said test and enabling inhalation of said personalized drug dosage, comprising:
    providing an adaptive personalized drug delivery apparatus configured to perform a spirometry test, determine a personalized drug dosage according to said test and enable inhalation of said personalized drug dosage, comprising:
    drug containing means;
    a spout configured to receive full lung exhalation of a user;
    a first tube connected with a second tube and a third tube through a valve defining a drug release mechanism;
    wherein said second tube is connected with said drug containing means; said third tube is connected with said spout; thereby said drug containing means being connected with said spout via said valve;
    a test mechanism comprising a sensor configured to perform said spirometry test by measuring said exhalation;
    an actuator configured to move said valve; and
    a controller connected with said test mechanism and said release mechanism;
    said controller configured to determine a personalized drug dosage according to said measured exhalation; actuate said actuator to direct said valve to open a path between said drug containing means and said spout, through said second tube said valve and said third tube, thereby enabling said user to inhale said determined personalized drug dosage; and redirect said valve to close said path between said drug containing means and said spout according to said determined personalized drug dosage and connect a path between said third tube and said first tube, stopping medicine flow from said drug containing means and re-enabling exhalation;
    receiving a user exhalation through said spout;
    measuring, by said sensor, said exhalation;

calculating and determining, by said controller, a personalized drug dosage for said user according to said measurement;

directing, by said controller, said valve to open the path between said drug containing means and said spout thereby enabling said user to inhale said determined personalized drug dosage; and redirecting, by said controller, said valve to close the path between said drug containing means and said spout thereby stopping medicine flow from said drug containing means according to said determined personalized drug dosage.

6. The method of claim 5, wherein said drug containing means comprise one of compartment, individual cells and strip.

7. The method of claim 5, wherein said drug containing means is replaceable.

8. The method of claim 7, wherein said replaceable drug containing means is a capsule.

* * * * *